(12) United States Patent
Chi Sing et al.

(10) Patent No.: US 8,814,775 B2
(45) Date of Patent: Aug. 26, 2014

(54) EXPANDABLE BRACHYTHERAPY APPARATUS AND METHODS FOR USING THEM

(75) Inventors: Eduardo Chi Sing, Dana Point, CA (US); Tommy G. Nguyen, Irvine, CA (US); Luis R. Urquidi, Oceanside, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 715 days.

(21) Appl. No.: 12/727,209

(22) Filed: Mar. 18, 2010

(65) Prior Publication Data

US 2011/0230700 A1    Sep. 22, 2011

(51) Int. Cl.
*A61N 5/00* (2006.01)
*A61M 29/02* (2006.01)
*A61N 5/10* (2006.01)
*A61M 25/10* (2013.01)

(52) U.S. Cl.
CPC .............. *A61N 5/1015* (2013.01); *A61M 29/02* (2013.01); *A61N 2005/1004* (2013.01); *A61M 25/10* (2013.01)
USPC ................... 600/3; 600/1; 600/7; 424/133.1; 424/450; 424/130.1

(58) Field of Classification Search
USPC ................. 600/7, 3, 1; 424/133.1, 450, 130.1
See application file for complete search history.

(56) References Cited

U.S. PATENT DOCUMENTS

| | | |
|---|---|---|
| 3,060,924 A | 10/1962 | Rush |
| 3,750,653 A | 8/1973 | Simon |
| 3,968,803 A | 7/1976 | Hyman |
| 4,427,005 A | 1/1984 | Tener |
| 4,580,561 A | 4/1986 | Williamson |
| 4,706,652 A | 11/1987 | Horowitz |
| 4,714,074 A | 12/1987 | Rey et al. |
| 4,798,212 A | 1/1989 | Arana |
| 4,936,823 A | 6/1990 | Colvin et al. |
| 4,957,476 A | 9/1990 | Cano |
| 4,976,680 A | 12/1990 | Hayman et al. |
| 5,056,523 A | 10/1991 | Hotchkiss, Jr. et al. |
| 5,106,360 A | 4/1992 | Ishiwara et al. |
| 5,152,741 A | 10/1992 | Farnio |
| 5,235,966 A | 8/1993 | Jamner |
| 5,242,372 A | 9/1993 | Carol |
| 5,279,565 A | 1/1994 | Klein et al. |
| 5,302,168 A | 4/1994 | Hess |
| 5,336,178 A | 8/1994 | Kaplan et al. |
| 5,354,257 A | 10/1994 | Roubin et al. |

(Continued)

*Primary Examiner* — Christine Matthews
*Assistant Examiner* — Sunita Reddy
(74) *Attorney, Agent, or Firm* — William A. English; Vista IP Law Group LLP

(57) ABSTRACT

Brachytherapy treatment apparatus are provided that include an elongate body including a core member and an outer member surrounding and movable relative to the core member. One or more helical catheters are provided on a distal portion of the elongate body, e.g., including distal ends coupled to the core member and proximal ends coupled to the outer member. The outer member is movable relative to the core member, e.g., axially and/or rotationally, to direct the helical catheters between a collapsed configuration for introduction through a tissue tract to a target location, e.g., a lumpectomy cavity, and an expanded configuration. Each helical catheter includes a lumen, and, after expansion to the expanded configuration, a source of radiation may be introduced along the helical catheters and/or a lumen of the core member for delivering radiation to the target location. Optionally, the apparatus may include a balloon surrounding or within the helical members.

33 Claims, 18 Drawing Sheets

(56) References Cited

U.S. PATENT DOCUMENTS

| | | | |
|---|---|---|---|
| 5,411,466 A | 5/1995 | Hess | |
| 5,423,747 A | 6/1995 | Amano | |
| 5,429,582 A | 7/1995 | Williams | |
| 5,429,605 A | 7/1995 | Richling et al. | |
| 5,484,384 A | 1/1996 | Fearnot | |
| 5,503,613 A | 4/1996 | Weinberger | |
| 5,509,900 A | 4/1996 | Kirkman | |
| 5,538,502 A | 7/1996 | Johnstone | |
| 5,540,659 A | 7/1996 | Teirstein | |
| 5,611,767 A | 3/1997 | Williams | |
| 5,653,683 A | 8/1997 | D'Andrea | |
| 5,678,572 A | 10/1997 | Shaw et al. | |
| 5,707,332 A | 1/1998 | Weinberger | |
| 5,713,828 A | 2/1998 | Coniglione | |
| 5,720,717 A | 2/1998 | D'Andrea | |
| 5,730,698 A | 3/1998 | Fischell et al. | |
| 5,782,740 A | 7/1998 | Schneiderman | |
| 5,840,008 A | 11/1998 | Klein et al. | |
| 5,843,163 A | 12/1998 | Wall | |
| 5,851,171 A | 12/1998 | Gasson | |
| 5,863,284 A | 1/1999 | Klein | |
| 5,882,291 A | 3/1999 | Bradshaw et al. | |
| 5,891,091 A | 4/1999 | Teirstein | |
| 5,910,102 A | 6/1999 | Hastings | |
| 5,913,813 A | 6/1999 | Williams et al. | |
| 5,916,143 A | 6/1999 | Apple et al. | |
| 5,931,774 A | 8/1999 | Williams et al. | |
| 5,938,582 A | 8/1999 | Ciamacco, Jr. et al. | |
| 5,942,209 A | 8/1999 | Leavitt et al. | |
| 5,976,106 A | 11/1999 | Verin et al. | |
| 6,013,019 A | 1/2000 | Fischell et al. | |
| 6,022,308 A | 2/2000 | Williams | |
| 6,030,333 A | 2/2000 | Sioshansi et al. | |
| 6,033,357 A | 3/2000 | Ciezki et al. | |
| 6,036,632 A | 3/2000 | Whitmore et al. | |
| 6,056,722 A | 5/2000 | Jayaraman | |
| 6,059,752 A | 5/2000 | Segal | |
| 6,071,263 A | 6/2000 | Kirkman | |
| 6,074,339 A | 6/2000 | Ganbale et al. | |
| 6,083,148 A | 7/2000 | Williams | |
| 6,117,064 A | 9/2000 | Apple et al. | |
| 6,117,065 A * | 9/2000 | Hastings et al. | 600/3 |
| 6,149,574 A | 11/2000 | Trauthen et al. | |
| 6,159,139 A | 12/2000 | Chiu | |
| 6,159,141 A | 12/2000 | Apple et al. | |
| 6,176,821 B1 | 1/2001 | Crocker et al. | |
| 6,179,766 B1 | 1/2001 | Dickerson | |
| 6,196,996 B1 | 3/2001 | Teirstein | |
| 6,200,256 B1 | 3/2001 | Weinberger | |
| 6,200,257 B1 | 3/2001 | Winkler | |
| 6,213,976 B1 | 4/2001 | Trerotola | |
| 6,217,585 B1 | 4/2001 | Houser et al. | |
| 6,221,003 B1 | 4/2001 | Sierocuk et al. | |
| 6,221,030 B1 | 4/2001 | Avaltroni | |
| 6,234,951 B1 | 5/2001 | Hastings | |
| 6,238,374 B1 | 5/2001 | Winkler | |
| 6,258,099 B1 | 7/2001 | Mareiro et al. | |
| 6,261,320 B1 | 7/2001 | Tam et al. | |
| 6,264,599 B1 | 7/2001 | Slater et al. | |
| 6,264,631 B1 | 7/2001 | Willis et al. | |
| 6,267,775 B1 | 7/2001 | Clerc et al. | |
| 6,283,911 B1 * | 9/2001 | Keren | 600/3 |
| 6,287,249 B1 | 9/2001 | Tam et al. | |
| 6,338,709 B1 | 1/2002 | Geoffrion | |
| 6,358,195 B1 | 3/2002 | Green et al. | |
| 6,371,904 B1 | 4/2002 | Sirimanne et al. | |
| 6,413,204 B1 | 7/2002 | Winkler et al. | |
| 6,458,069 B1 | 10/2002 | Tam et al. | |
| 6,482,142 B1 | 11/2002 | Winkler et al. | |
| 6,482,178 B1 | 11/2002 | Andrews et al. | |
| 6,494,824 B1 | 12/2002 | Apple et al. | |
| 6,506,145 B1 | 1/2003 | Bradshaw et al. | |
| 6,508,784 B1 | 1/2003 | Shu | |
| 6,527,692 B1 | 3/2003 | Weinberger | |
| 6,527,693 B2 | 3/2003 | Munro, III et al. | |
| 6,537,194 B1 | 3/2003 | Winkler | |
| 6,540,656 B2 | 4/2003 | Fontayne et al. | |
| 6,540,734 B1 | 4/2003 | Chiu et al. | |
| 6,554,757 B1 | 4/2003 | Geitz | |
| 6,582,353 B1 | 6/2003 | Hastings et al. | |
| 6,589,158 B2 | 7/2003 | Winkler | |
| 6,592,548 B2 | 7/2003 | Jayaraman | |
| 6,607,476 B1 | 8/2003 | Barnhart | |
| 6,607,478 B2 | 8/2003 | Williams | |
| 6,638,206 B2 | 10/2003 | Green et al. | |
| 6,641,518 B2 | 11/2003 | Wolfson et al. | |
| 6,645,135 B1 | 11/2003 | Bhat | |
| 6,648,811 B2 | 11/2003 | Sierocuk et al. | |
| 6,659,933 B2 | 12/2003 | Asano | |
| 6,673,006 B2 | 1/2004 | Winkler | |
| 6,676,667 B2 | 1/2004 | Mareiro et al. | |
| 6,685,619 B2 | 2/2004 | Halpern et al. | |
| 6,692,460 B1 | 2/2004 | Jayaraman | |
| 6,699,170 B1 | 3/2004 | Crocker et al. | |
| 6,746,465 B2 | 6/2004 | Diederich et al. | |
| 6,752,752 B2 | 6/2004 | Geitz | |
| 6,910,999 B2 | 6/2005 | Chin et al. | |
| 6,923,754 B2 | 8/2005 | Lubock | |
| 6,955,641 B2 | 10/2005 | Lubock | |
| 7,041,047 B2 | 5/2006 | Gellman et al. | |
| 7,056,276 B2 | 6/2006 | Nakano et al. | |
| 7,357,770 B1 | 4/2008 | Cutrer et al. | |
| 7,413,539 B2 | 8/2008 | Lubock | |
| 7,465,268 B2 | 12/2008 | Lubock | |
| 2001/0007071 A1 | 7/2001 | Koblish | |
| 2002/0016583 A1 | 2/2002 | Cragg | |
| 2002/0032359 A1 | 3/2002 | Geoffrion et al. | |
| 2002/0165427 A1 | 11/2002 | Yachia et al. | |
| 2002/0193735 A1 * | 12/2002 | Stiger | 604/101.01 |
| 2002/0198432 A1 * | 12/2002 | Stiger et al. | 600/3 |
| 2003/0092957 A1 | 5/2003 | Scott et al. | |
| 2003/0114878 A1 | 6/2003 | Diederich et al. | |
| 2003/0158515 A1 | 8/2003 | Gonzalez et al. | |
| 2003/0163017 A1 | 8/2003 | Tam et al. | |
| 2003/0236443 A1 | 12/2003 | Cespedes et al. | |
| 2004/0006305 A1 | 1/2004 | Hebert et al. | |
| 2004/0068231 A1 | 4/2004 | Blondeau | |
| 2004/0087828 A1 | 5/2004 | Green et al. | |
| 2004/0116767 A1 | 6/2004 | Lebovic et al. | |
| 2004/0127765 A1 | 7/2004 | Seiler et al. | |
| 2004/0158158 A1 * | 8/2004 | Mawad | 600/3 |
| 2004/0260142 A1 | 12/2004 | Lovoi | |
| 2005/0061533 A1 | 3/2005 | Lovoi et al. | |
| 2005/0075662 A1 | 4/2005 | Pedersen et al. | |
| 2005/0080313 A1 | 4/2005 | Stewart et al. | |
| 2005/0090845 A1 | 4/2005 | Boyd | |
| 2005/0096647 A1 | 5/2005 | Steinke et al. | |
| 2005/0101823 A1 | 5/2005 | Linares et al. | |
| 2005/0101860 A1 | 5/2005 | Patrick et al. | |
| 2005/0124843 A1 | 6/2005 | Singh | |
| 2005/0182286 A1 | 8/2005 | Lubock | |
| 2005/0240074 A1 | 10/2005 | Lubock | |
| 2006/0015166 A1 | 1/2006 | Kindlein et al. | |
| 2006/0020156 A1 | 1/2006 | Shukla | |
| 2006/0094923 A1 | 5/2006 | Mate | |
| 2006/0100475 A1 * | 5/2006 | White et al. | 600/3 |
| 2006/0116546 A1 | 6/2006 | Eng | |
| 2006/0173233 A1 | 8/2006 | Lovoi | |
| 2006/0173235 A1 | 8/2006 | Lim et al. | |
| 2006/0184192 A1 | 8/2006 | Markworth et al. | |
| 2006/0199990 A1 | 9/2006 | Rioux et al. | |
| 2006/0235365 A1 | 10/2006 | Terwilliger et al. | |
| 2006/0258895 A1 | 11/2006 | Maschke | |
| 2007/0106108 A1 | 5/2007 | Hermann et al. | |
| 2007/0142694 A1 | 6/2007 | Cutrer et al. | |
| 2007/0167665 A1 | 7/2007 | Hermann | |
| 2007/0167666 A1 | 7/2007 | Lubock | |
| 2007/0167667 A1 | 7/2007 | Lubock et al. | |
| 2007/0191668 A1 | 8/2007 | Lubock et al. | |
| 2007/0270627 A1 * | 11/2007 | Cutrer et al. | 600/7 |
| 2008/0091055 A1 * | 4/2008 | Nguyen et al. | 600/7 |
| 2008/0177127 A1 * | 7/2008 | Allan et al. | 600/7 |

(56) References Cited

U.S. PATENT DOCUMENTS

| | | | |
|---|---|---|---|
| 2008/0221384 A1* | 9/2008 | Chi Sing et al. | 600/7 |
| 2008/0228025 A1 | 9/2008 | Quick | |
| 2009/0156882 A1 | 6/2009 | Chi Sing | |
| 2010/0048978 A1 | 2/2010 | Chi Sing | |
| 2012/0059210 A1* | 3/2012 | Frassica | 600/3 |

* cited by examiner

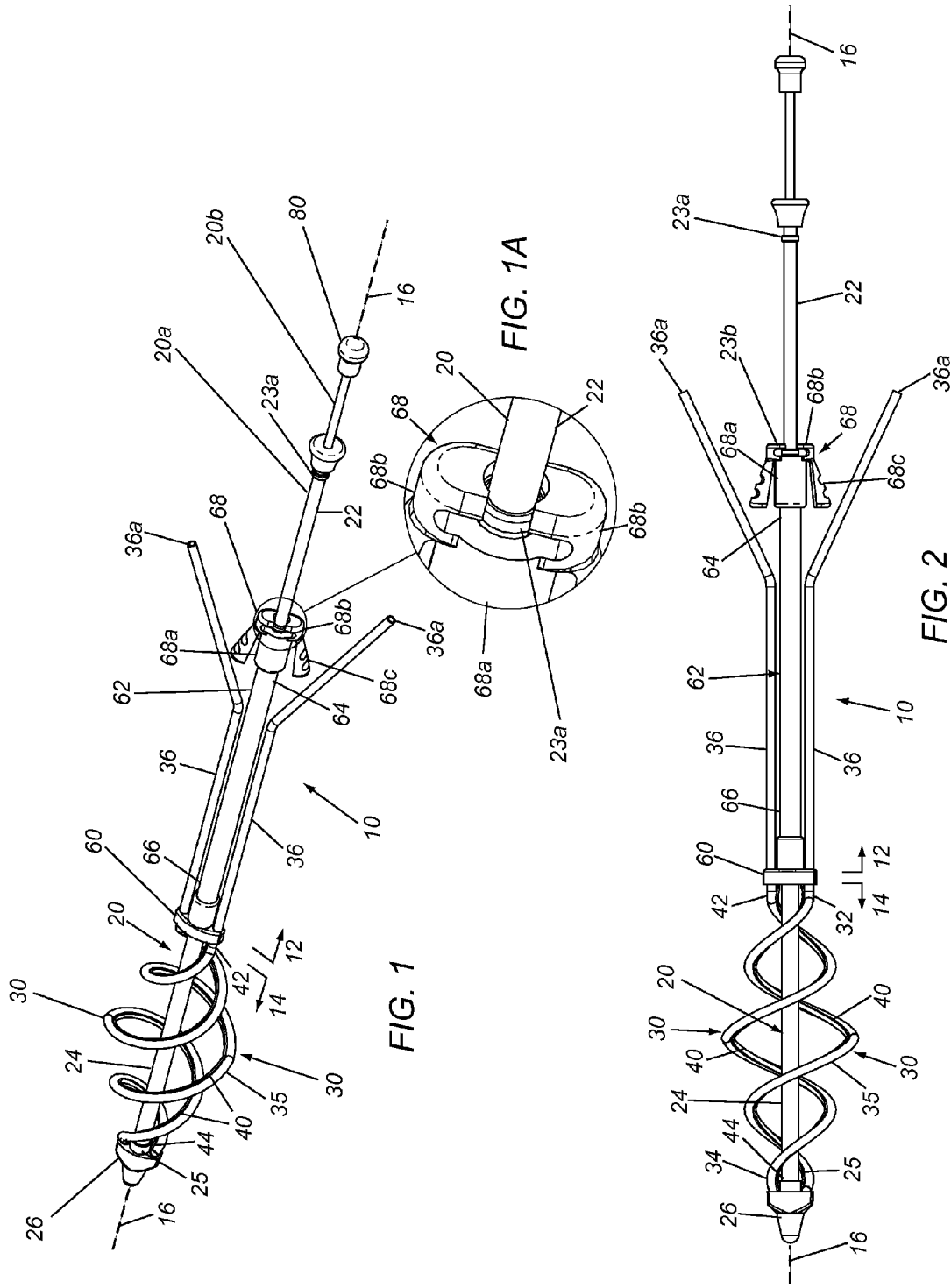

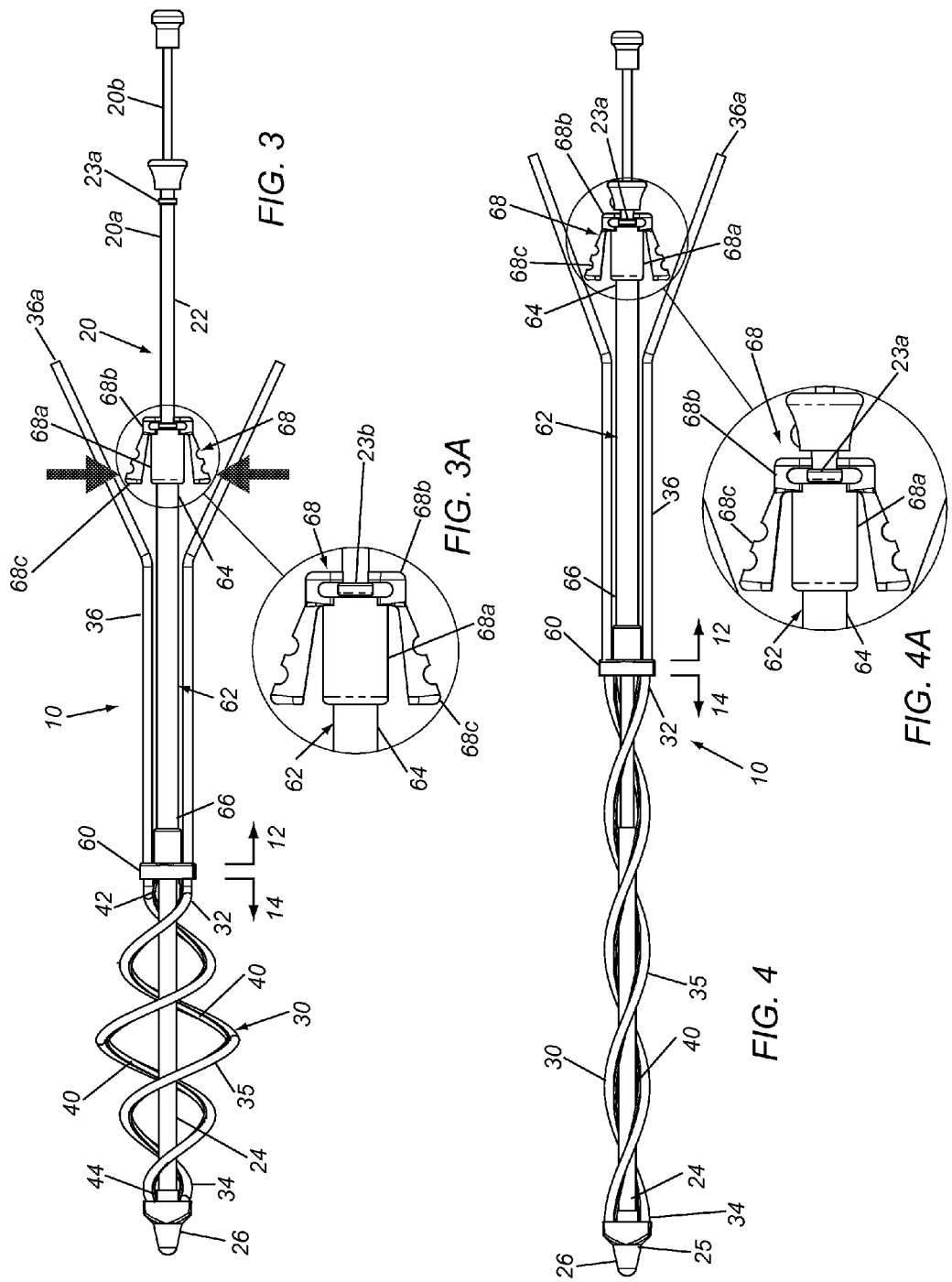

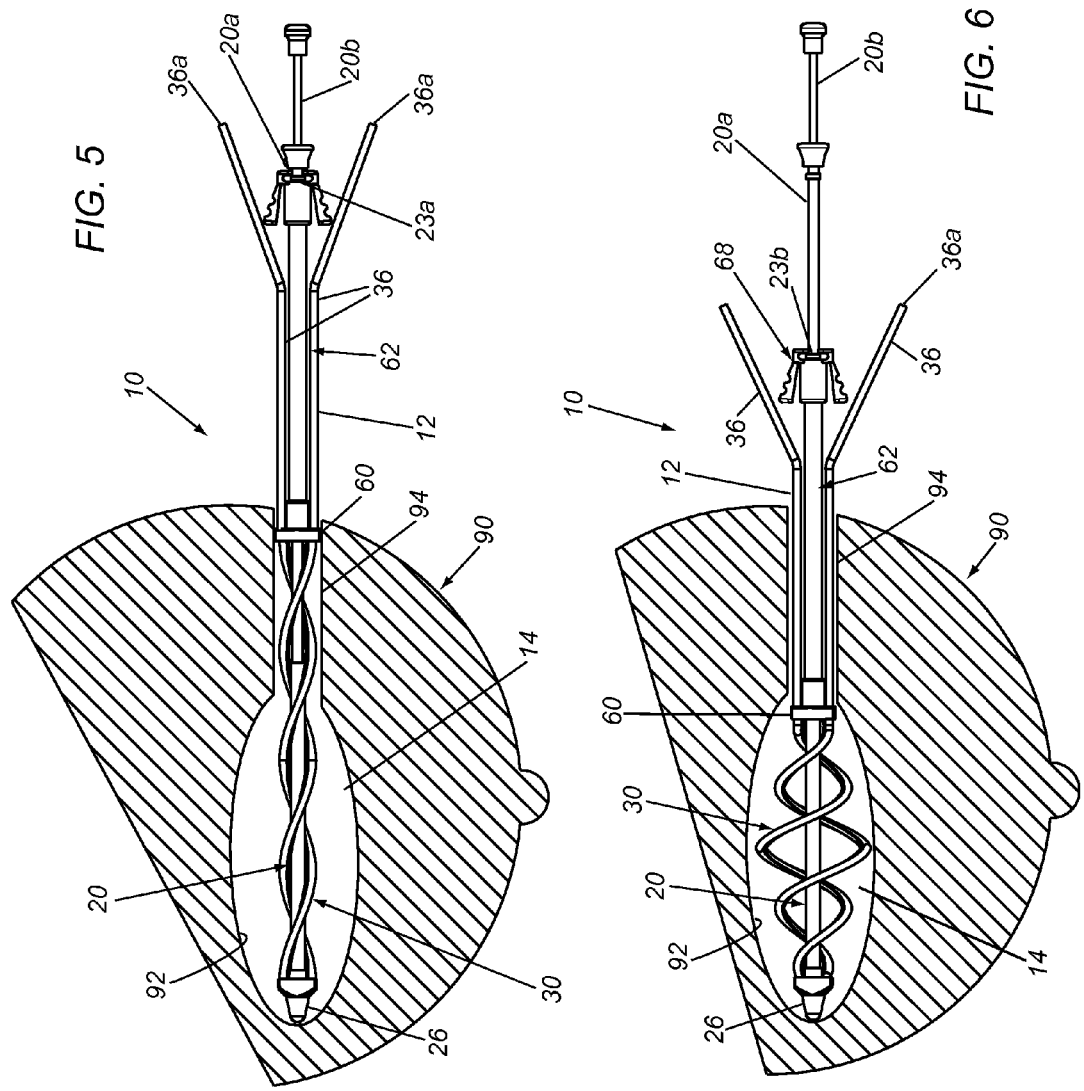

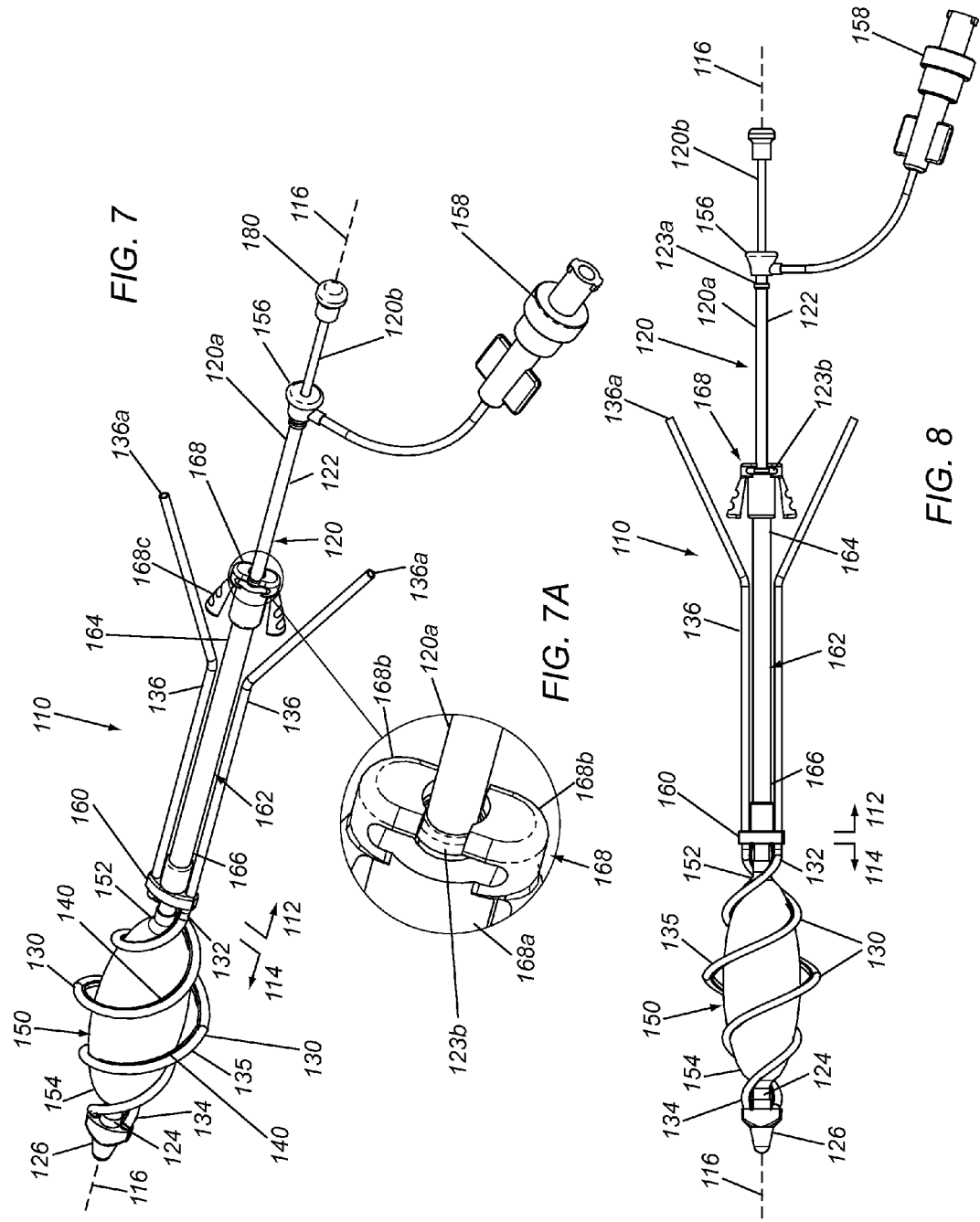

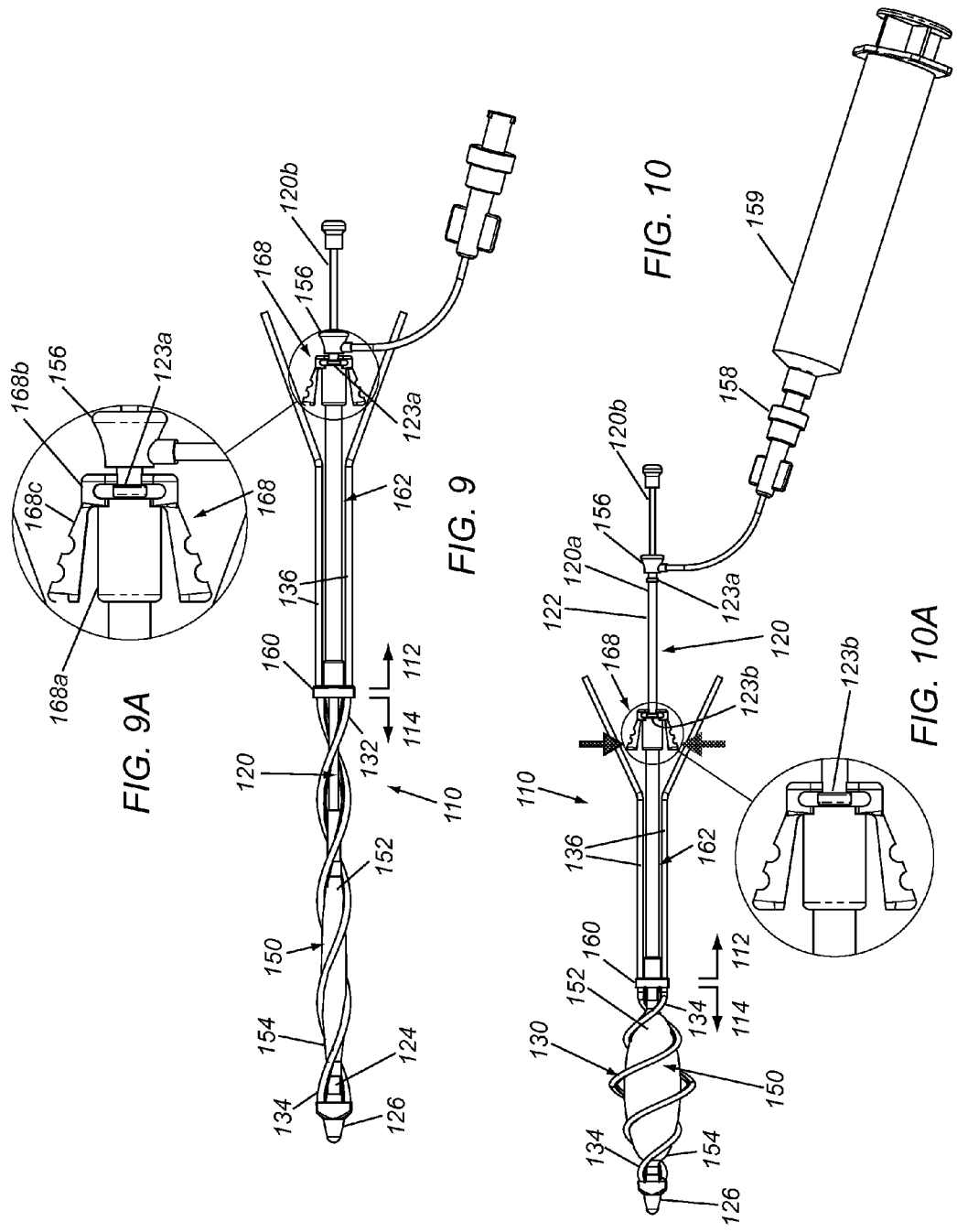

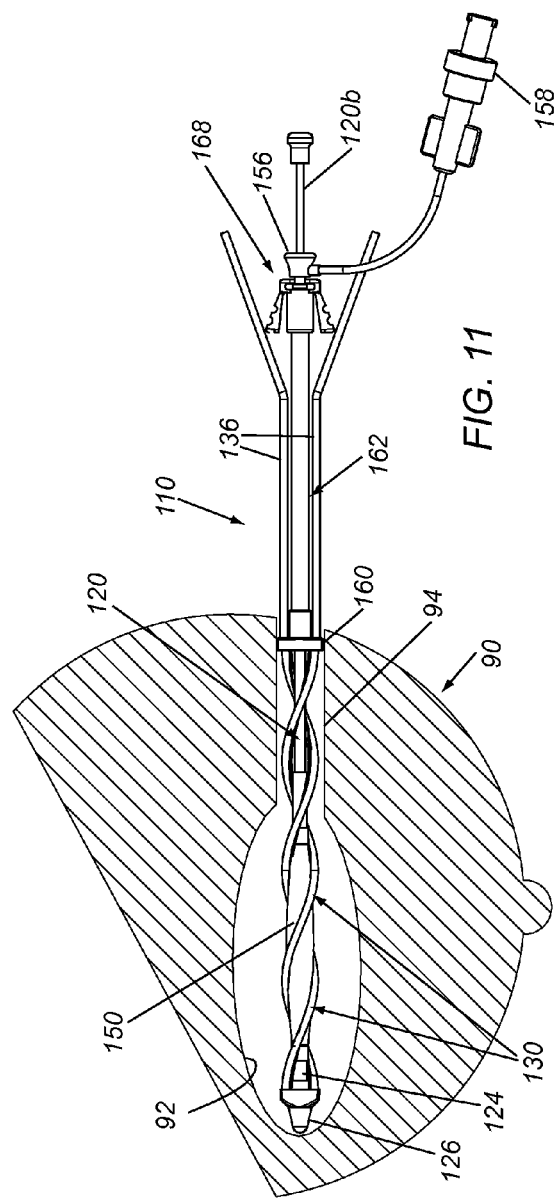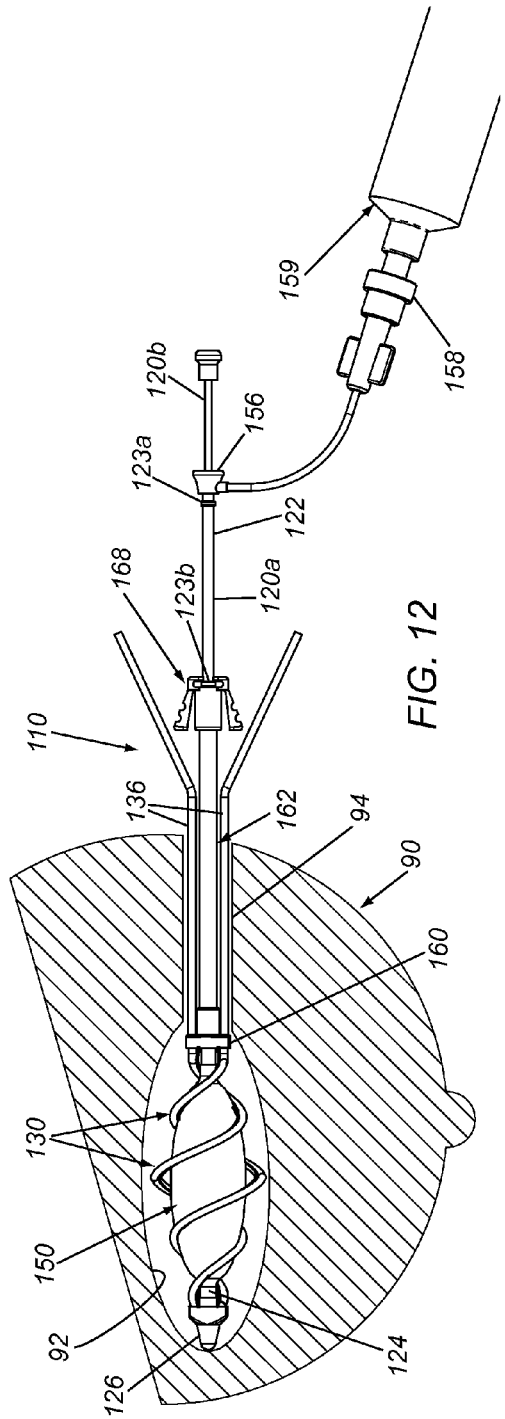

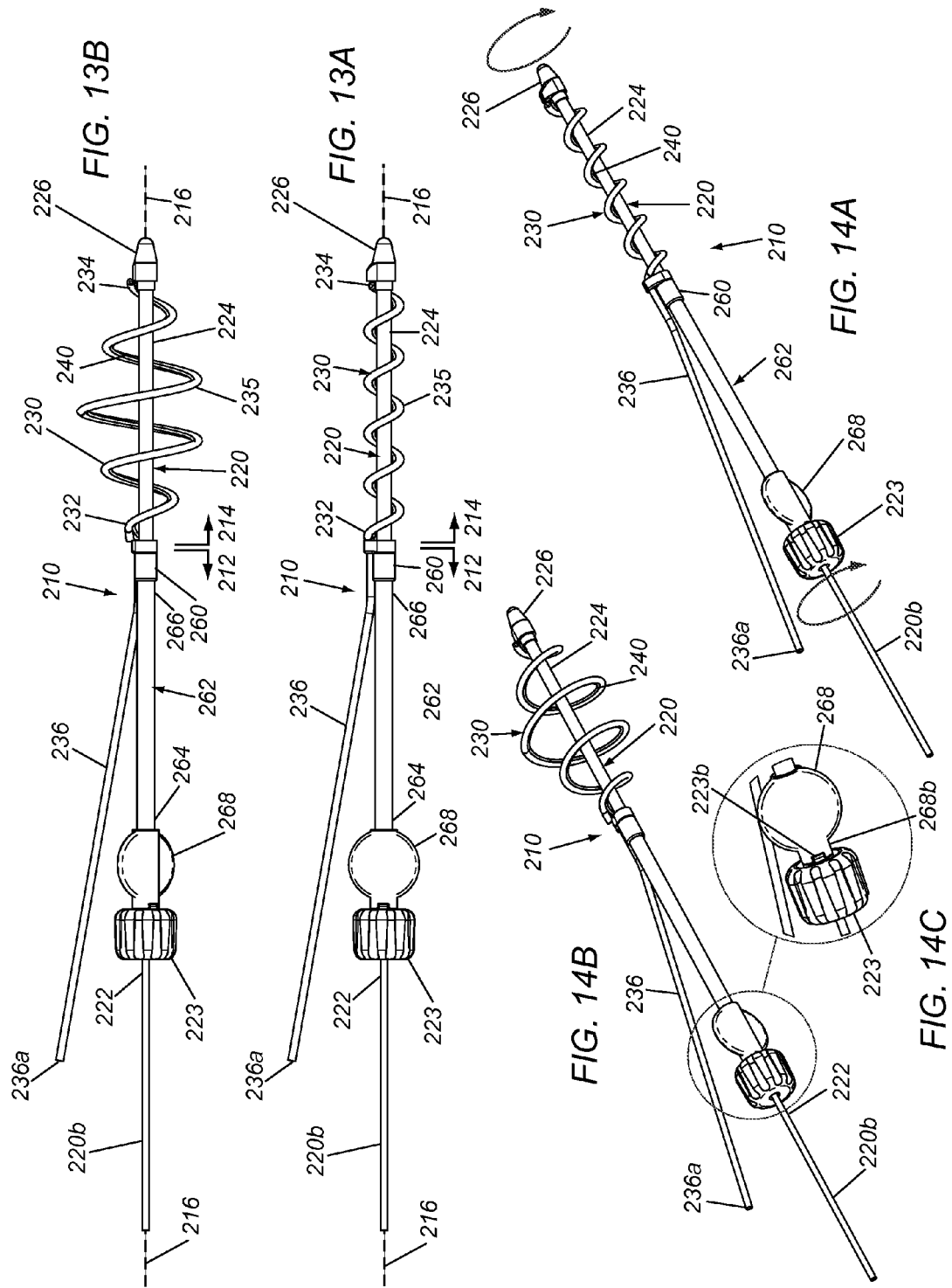

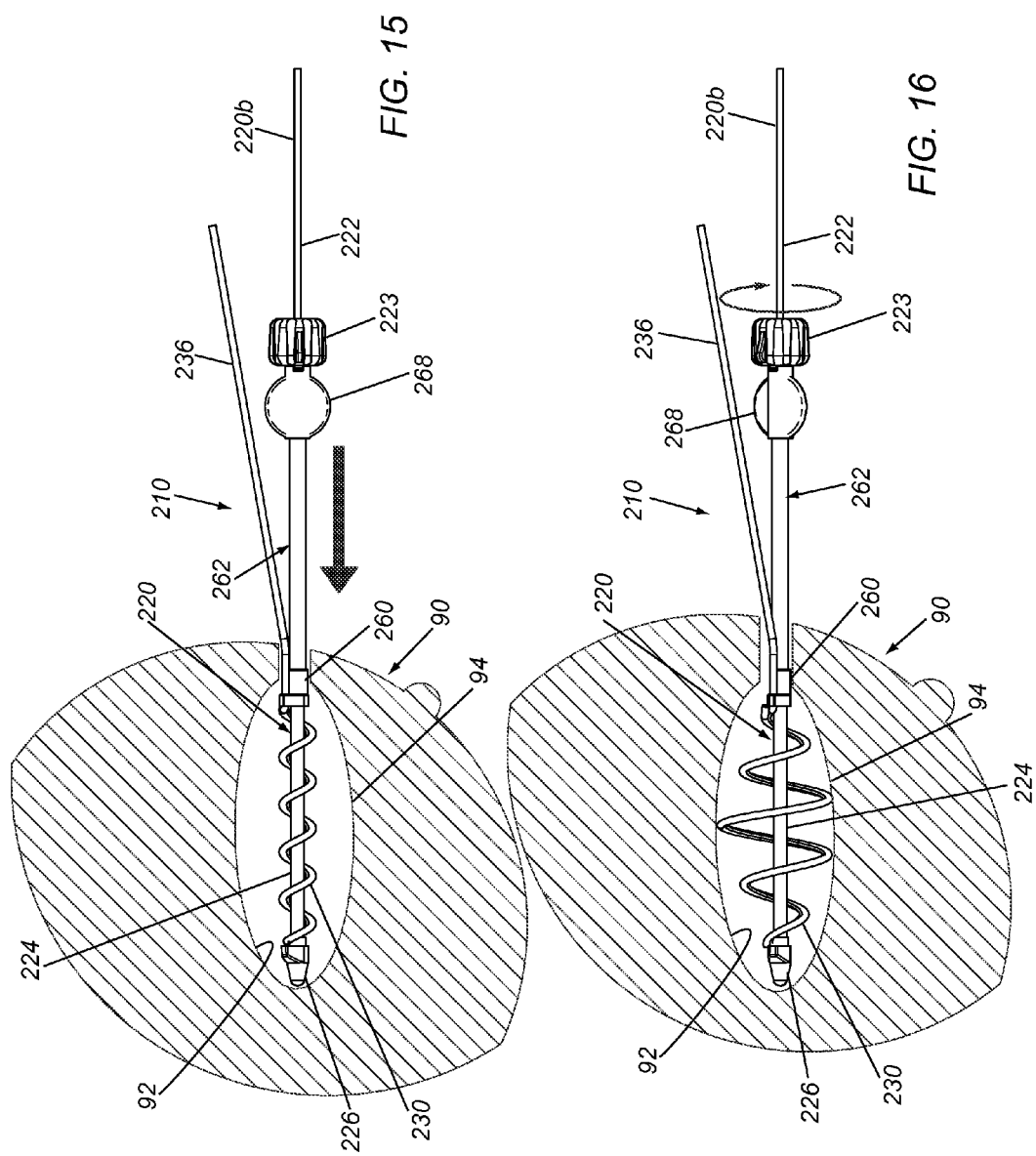

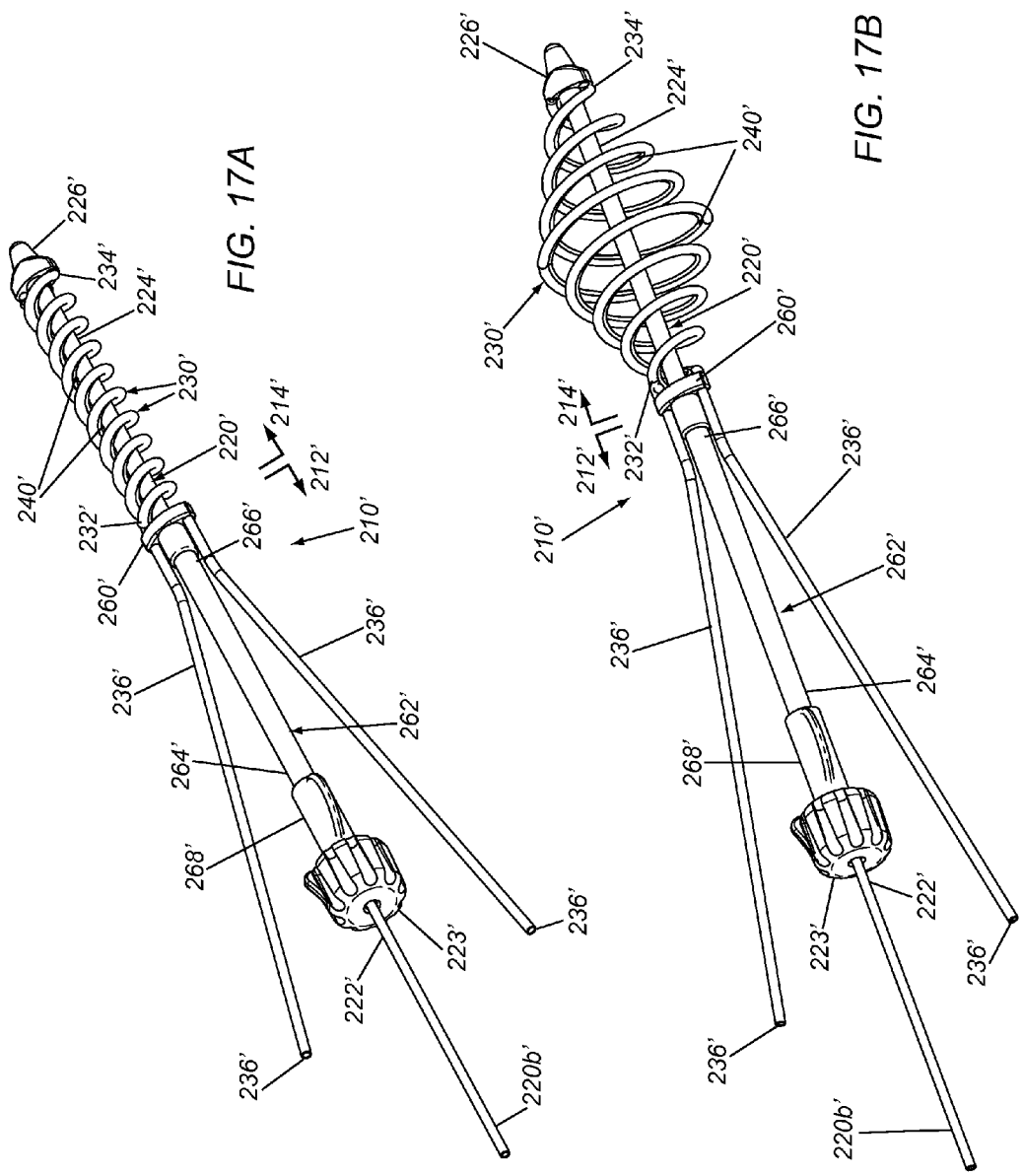

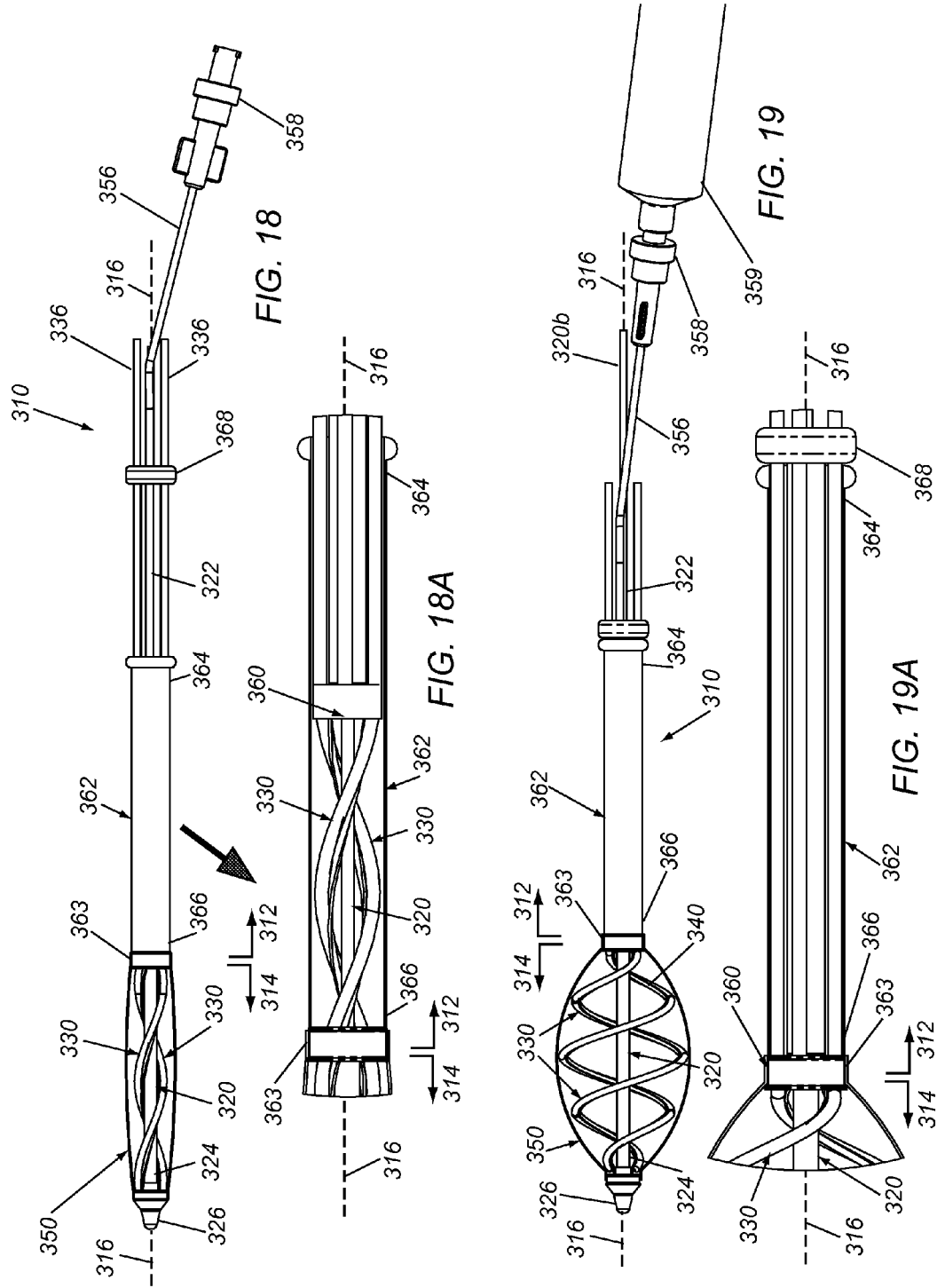

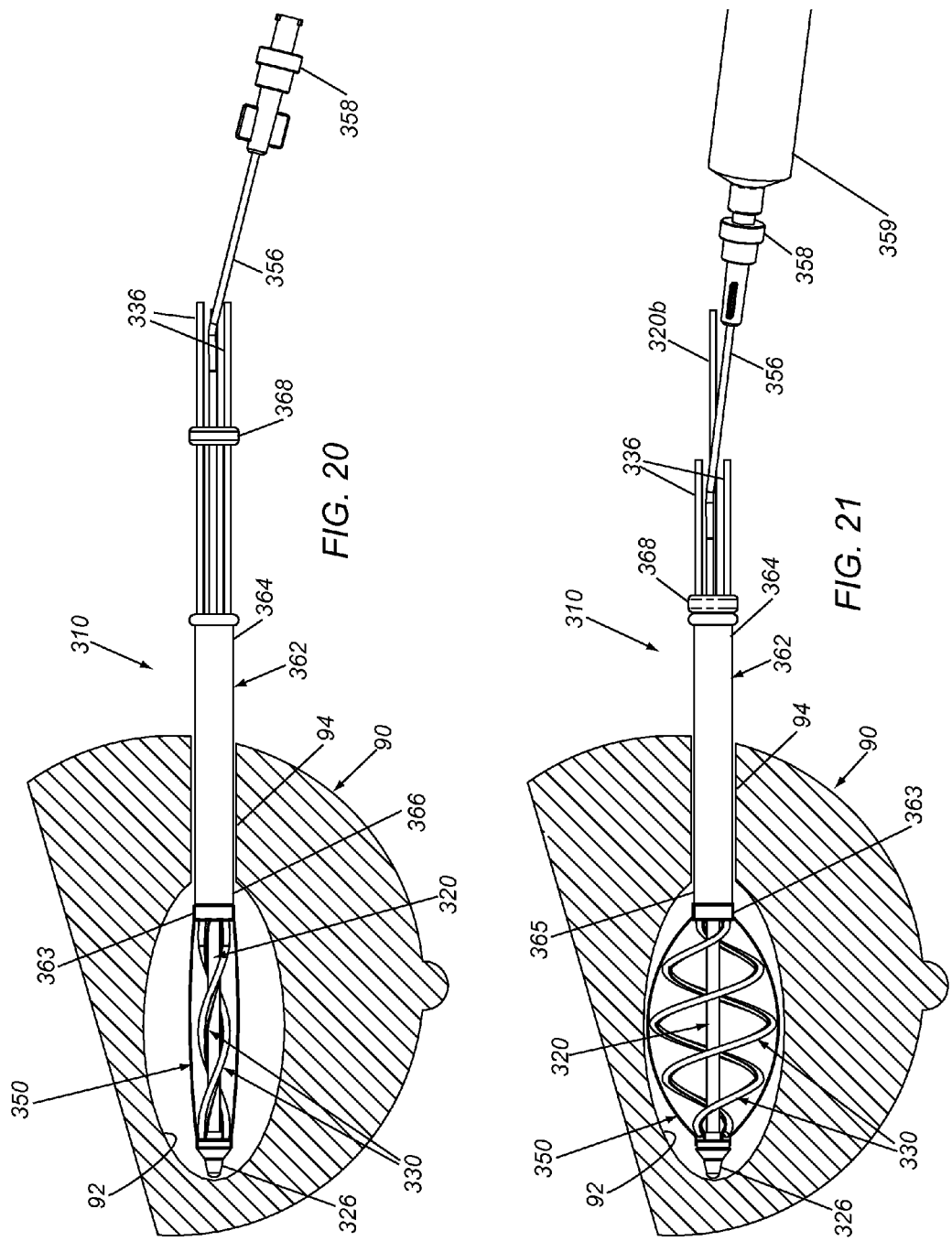

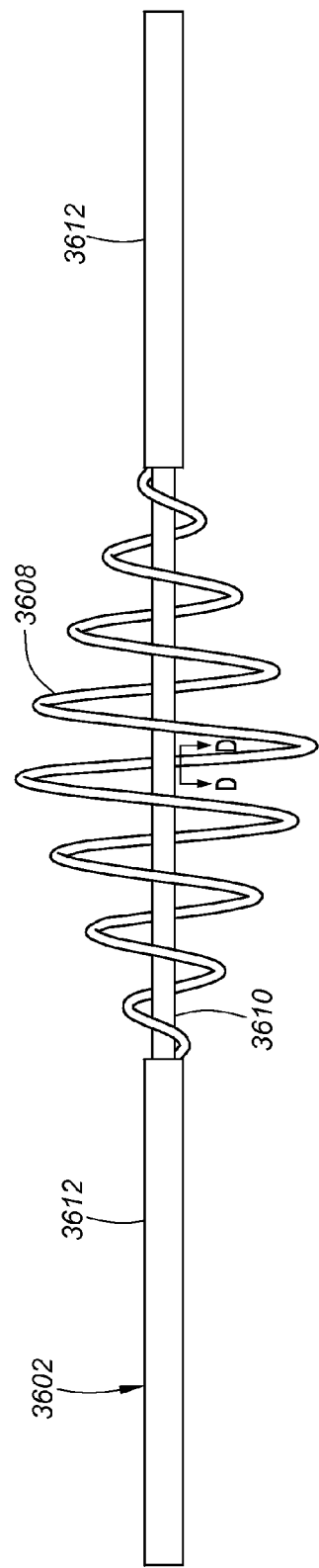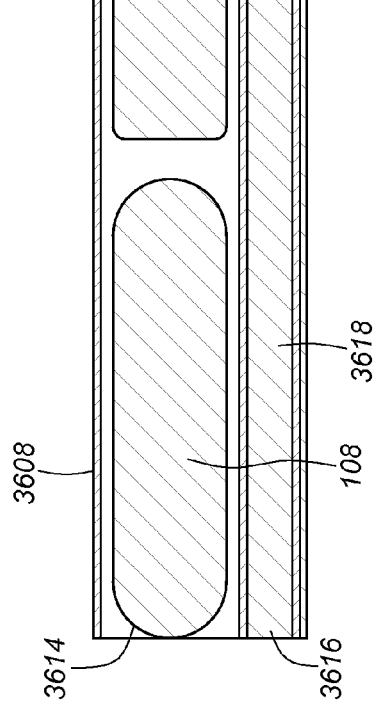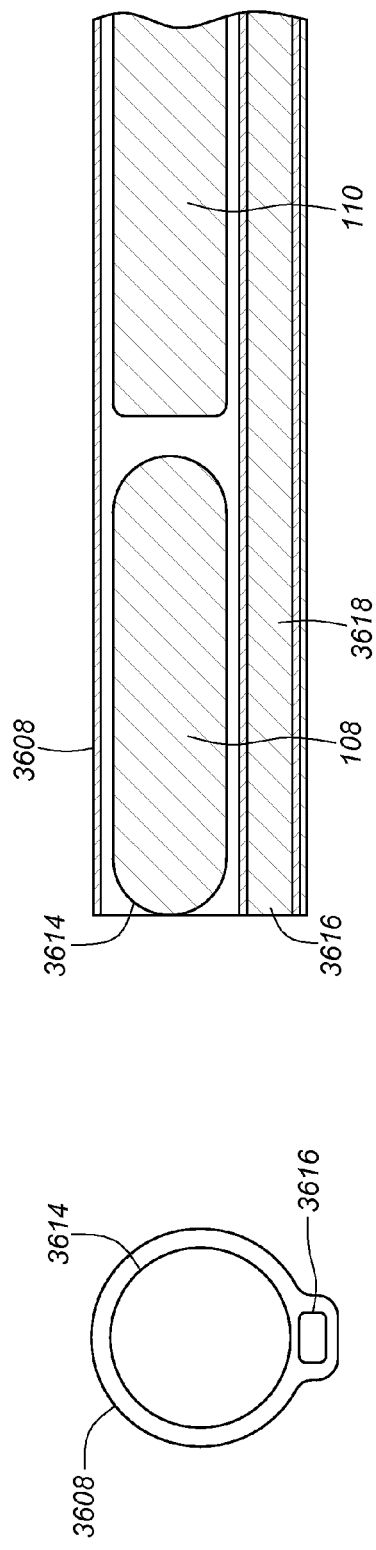
FIG. 23C
FIG. 23E
FIG. 23D

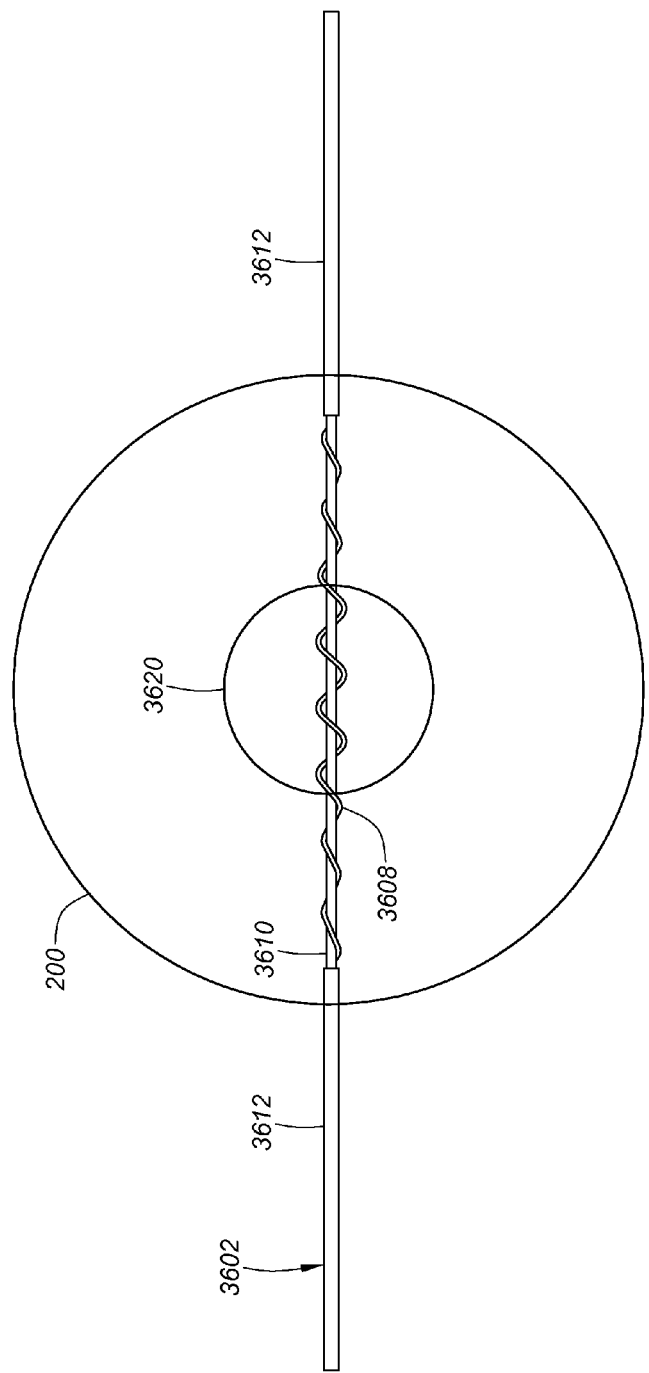

EXPANDABLE BRACHYTHERAPY APPARATUS AND METHODS FOR USING THEM

FIELD OF THE INVENTION

The present invention relates generally to apparatus, systems, and methods for providing brachytherapy to a human or other mammalian body, and more particularly to expandable apparatus for performing brachytherapy treatment within tissue, e.g., within breast tissue and/or within a body cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, which may include a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In contrast, LDR brachytherapy involves placing a low activity radiation source into the target tissue for a longer, sometimes indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also, there are radiobiological advantages of LDR brachytherapy over HDR brachytherapy (e.g., the dose rate effect), which may lead to better sparing of normal tissue during treatment. Moreover, for patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

While effective, current brachytherapy implementations have potential drawbacks. For example, LDR seeds are typically left indwelling and free floating within the target tissue and are, therefore, susceptible to migration. Moreover, once implanted, LDR seeds are generally not considered removable or repositionable. LDR brachytherapy may also require careful dose distribution calculations and seed mapping before, and often during, seed implantation. Such calculation and mapping may allow effective radiation delivery to the target tissue volume, while minimizing radiation to surrounding healthy tissue (e.g., the urethra and rectum, for example, in prostate brachytherapy). Yet, while such dose calculation and seed mapping techniques are effective, problems may exist, such as potentially significant variability in accuracy of seed placement among different clinicians.

Yet another issue with conventional LDR brachytherapy techniques is that they may require the radioactive seeds to be manipulated individually at the time of implantation, which may be a time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus, systems, and methods for delivering brachytherapy to a localized target tissue region. While potentially useful in treating most any area of the body, an exemplary application is treating breast tissue, e.g., breast tumors or lumpectomy cavities. For example, the apparatus may be used to place and remove a localized radiation source for both neoadjuvant and post-excisional treatment.

In accordance with one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period of time (e.g., in LDR applications). In either instance, the radiation sources may deliver therapy to the target tissue region in accordance with a predefined therapy profile.

In some embodiments, LDR radiation sources may be implanted and secured to the body or target tissue in such a way as to prevent or substantially limit movement of the sources relative to the target tissue. For example, the apparatus and methods described herein may facilitate indwelling therapy using pre-arranged packages of radioactive sources, e.g., seeds, but also allow easy removal of the radiation sources upon completing brachytherapy treatment.

As used herein, "radiation source" and "radioactive source" may include any therapeutic element operable to deliver a dose of radiation. For example, the radiation source may be one or more radioactive seeds or, alternatively, one or more LDR or HDR wire elements (e.g., Iridium wire), e.g., as disclosed in the applications incorporated by reference elsewhere herein.

The term "implantable," as used herein, indicates the capability of a device to be inserted into the body and then maintained in a relatively fixed or static position within the surrounding tissue for an extended period of time, e.g., an hour or more and/or several hours or more, including several days or more.

Furthermore, "target tissue," "target tissue region," "target region," and "target tissue volume," as used herein, may include any portion of a human (or other mammalian) body that has been identified to benefit from radiation therapy. For example, the target tissue region may be a tumor or lesion itself, tissue proximate or surrounding the tumor, or a cavity region created by tumor excision (such as the surrounding tissue or cavity associated with a lumpectomy cavity of the breast).

It should be noted that the apparatus, systems, and methods described herein may be used for LDR or HDR brachytherapy, as described elsewhere herein and in the applications incorporated by reference herein. Moreover, while described herein with respect to brachytherapy, the apparatus, systems, and methods may apply to other therapy regimens that benefit from the removable implantation of therapy-delivering elements. In an exemplary application, the apparatus, systems, and methods are described herein for treating breast cancer. However, it will be appreciated that the apparatus, systems, and methods described herein may be used for treating other cancers or conditions that may benefit from brachytherapy treatment.

In accordance with one embodiment, a brachytherapy treatment apparatus is provided that includes an elongate body including a proximal end and a distal end sized for introduction into a tract through tissue. One or more elongate helical members may be provided on the distal end including pathway(s) for receiving a source of radiation therealong, the helical member(s) being movable between a collapsed configuration for introduction through a tissue tract to a target location and an expanded helical configuration. A source of radiation may be introduceable along the pathway(s) when the helical member(s) for delivering radiation to the target location.

In an exemplary embodiment, the elongate body may include a core member including proximal and distal ends, and an outer member surrounding and movable relative to the core member. Distal end(s) of the helical member(s) may be coupled to the core member distal end, and proximal end(s) of the helical member(s) may be coupled to the outer member such that movement of the outer member relative to the core member, e.g., axially and/or rotationally, directs the helical member(s) between the collapsed and expanded configurations. The helical member(s) may extend around the core member one or more times such that the helical member(s) is(are) disposed against or otherwise immediately adjacent the core member in the collapsed configuration and spaced apart from the core member in the expanded configuration.

In one embodiment, only one elongate helical member may be provided on the distal end of the elongate body. In another embodiment, a pair of helical members may be provided on the distal end, e.g., that are offset from one another around the elongate body, e.g., by one hundred eighty degrees (180°), and/or that extend helically in the same direction such that the helical members do not overlap one another. Optionally, more than two helical members may be provided that are offset from one another and/or that extend helically in the same direction such that the helical members do not overlap one another.

Thus, the one or more helical members may provide one or more helical pathways, e.g., lumens, for receiving a radiation source therealong. Optionally, the core member may also include a lumen to provide a central pathway for receiving a radiation source.

In accordance with another embodiment, a method is provided for brachytherapy treatment of tissue within a body that includes creating a tract through tissue to a target location comprising a cavity, and advancing an elongate body carrying one or more elongate helical members through the tract into the target location with the helical member(s) in a collapsed configuration. The helical member(s) may be directed to an expanded helical configuration at the target location to position the helical member(s) away from a central axis, and radiation may be delivered to the target location via the helical member(s) to treat tissue at the target location.

In accordance with still another embodiment, a system for brachytherapy treatment of tissue adjacent a cavity within a body is provided that includes an expandable brachytherapy apparatus and one or more sources of radiation, such as a HDR radiation source. The apparatus may include an elongate body including proximal and distal ends, and one or more elongate helical members on the distal end including pathways for receiving the source(s) of radiation therealong. The helical member(s) may be movable between a collapsed configuration for introduction through a tissue tract to a target location and an expanded helical configuration for delivery of radiation using the source(s) of radiation.

In accordance with yet another embodiment, a brachytherapy treatment apparatus is provided that includes an elongate core member including a proximal end and a distal end configured for introduction into a tract through tissue and terminating in a distal tip; an outer member surrounding a portion of the core member proximal to the distal tip and movable relative to the core member; an expandable member surrounding at least a portion of the core member distal end; and one or more helical members on the distal end. Each helical member may include a distal end coupled to the core member distal end, a proximal end coupled to the outer member, an elongate portion that extends helically around the core member between the helical member proximal and distal ends, and a pathway extending between the helical member proximal and distal ends for receiving a source of radiation therealong. The outer member may be actuatable for moving the one or more helical members from a collapsed configuration to an expanded configuration such that each elongate portion is directed radially outwardly away from the core member.

In one embodiment, the expandable member may surround the one or more helical members, while in another embodiment, the one or more helical members may extend helically around an outer surface of the expandable member. The expandable member may be expandable independently of or substantially simultaneously with the one or more helical members.

In accordance with still another embodiment, a method is provided for brachytherapy treatment of tissue within a body that includes creating a tract through tissue to a target location adjacent to a cavity; advancing an elongate body carrying one or more elongate helical members through the tract into the target location with the helical members in a collapsed configuration; directing the one or more helical members to an expanded configuration at the target location to position the one or more helical members away from a central axis; and delivering radiation to the target location to treat tissue at the target location.

In accordance with yet another embodiment, a method is provided for brachytherapy treatment of tissue that includes advancing a distal end of an elongate body through tissue into a body cavity, the distal end carrying an expandable member and one or more elongate helical members in a collapsed configuration; expanding the expandable member within the body cavity; and directing the one or more helical members to an expanded configuration within the body cavity to position the one or more helical members away from a central axis. One or more radiation sources may be delivered into the body cavity via the one or more helical members and/or the core member to treat tissue adjacent the body cavity.

In an exemplary embodiment, the expandable member may surround the one or more helical members and the expandable member may be expanded before directing the one or more helical members to the expanded configuration. In the expanded configuration, the one or more helical members may be spaced inwardly away from the expandable member or may contact the expandable member. Alternatively, the one or more helical members may extend helically around an outer surface of the expandable member, and wherein the expandable member is expanded after directing the one or more helical members to the expanded configuration.

The above summary is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The drawings illustrate exemplary embodiments, in which:

FIG. 1 is a perspective view of a first exemplary embodiment of a brachytherapy apparatus including an expandable therapy delivery portion that includes a pair of helical catheter members in an expanded configuration.

FIG. 1A is a detail of detents on the apparatus of FIG. 1 for releasably securing the apparatus in the expanded configuration.

FIG. 2 is a side view of the apparatus of FIG. 1 in the expanded configuration.

FIGS. 3 and 4 are side views of the apparatus of FIG. 1 in expanded and collapsed configurations, respectively.

FIGS. 3A and 4A are details of detents on the apparatus of FIGS. 3 and 4 for releasably securing the apparatus in the expanded and collapsed configurations, respectively.

FIGS. 5 and 6 are cross-sectional views of a breast, showing the apparatus of FIGS. 1-4 being introduced into a lumpectomy cavity in the breast in the collapsed configuration (FIG. 5) and expanded to the expanded configuration (FIG. 6).

FIG. 7 is a perspective view of a second exemplary embodiment of a brachytherapy apparatus including an expandable therapy delivery portion that includes a pair of helical members and a balloon, with the helical members and balloon in an expanded configuration.

FIG. 7A is a detail of detents on the apparatus of FIG. 7 releasably securing the apparatus in the expanded configuration.

FIG. 8 is a side view of the apparatus of FIG. 7 with the helical members and balloon in the expanded configuration.

FIG. 9 is a side view of the apparatus of FIGS. 7-8 with the helical members and balloon in a collapsed configuration.

FIG. 9A is a detail of detents on the apparatus of FIG. 9 releasably securing the apparatus in the collapsed configuration.

FIG. 10 is a side view of the apparatus of FIGS. 7-8 in the expanded configuration and showing a syringe for inflating a balloon.

FIG. 10A is a detail of detents on the apparatus of FIG. 10 releasably securing the apparatus in the expanded configuration.

FIGS. 11 and 12 are cross-sectional views of a breast, showing the apparatus of FIGS. 7-10 being introduced into a lumpectomy cavity in the breast in the collapsed configuration (FIG. 11) and expanded to the expanded configuration (FIG. 12).

FIGS. 13A and 13B are side views of a third exemplary embodiment of a brachytherapy apparatus including an expandable therapy delivery portion that includes a helical catheter member in collapsed and expanded configurations, respectively.

FIGS. 14A and 14B are perspective views of the apparatus shown in FIGS. 13A and 13B, respectively.

FIG. 14C is a detail of detents on the apparatus of FIGS. 13-14 for releasably securing the apparatus in the expanded configuration.

FIGS. 15 and 16 are cross-sectional views of a breast, showing the apparatus of FIGS. 13-14 being introduced into a lumpectomy cavity in the breast in the collapsed configuration (FIG. 15) and expanded to the expanded configuration (FIG. 16).

FIGS. 17A and 17B are perspective views of a fourth exemplary embodiment of a brachytherapy apparatus including an expandable therapy delivery portion that includes a pair of helical catheter members in collapsed and expanded configurations, respectively.

FIGS. 18 and 19 are side views of a fifth exemplary embodiment of a brachytherapy apparatus including an expandable therapy delivery portion that includes a pair of helical catheter members disposed within a balloon in collapsed and expanded configurations, respectively.

FIGS. 18A and 19A are cross-sectional details of an actuator of the apparatus of FIGS. 18 and 19 in first and second positions, respectively, for directing the catheter members between the collapsed and expanded configurations.

FIGS. 20-22 are cross-sectional views of a breast, showing the apparatus of FIGS. 18-19 being introduced into a lumpectomy cavity in the breast in the collapsed configuration (FIG. 20) and expanded to the expanded configuration (FIGS. 21, 22).

FIGS. 23B and 23C are perspective and side views, respectively, of the apparatus of FIG. 23A in an expanded configuration.

FIG. 23D is a cross section of the helical catheter member of the apparatus of FIGS. 23A-23C taken along line D-D of FIG. 23C.

FIG. 23E is a longitudinal cross-sectional view of the helical catheter member of the apparatus of FIGS. 23A-D.

FIGS. 23F and 23G are cross-sectional views of a breast, showing the apparatus of FIGS. 23A-23C introduced into a lumpectomy cavity in the breast in the collapsed configuration (FIG. 23F) and expanded to the expanded configuration (FIG. 23G).

DETAILED DESCRIPTION OF EXEMPLARY EMBODIMENTS

Figure 22:
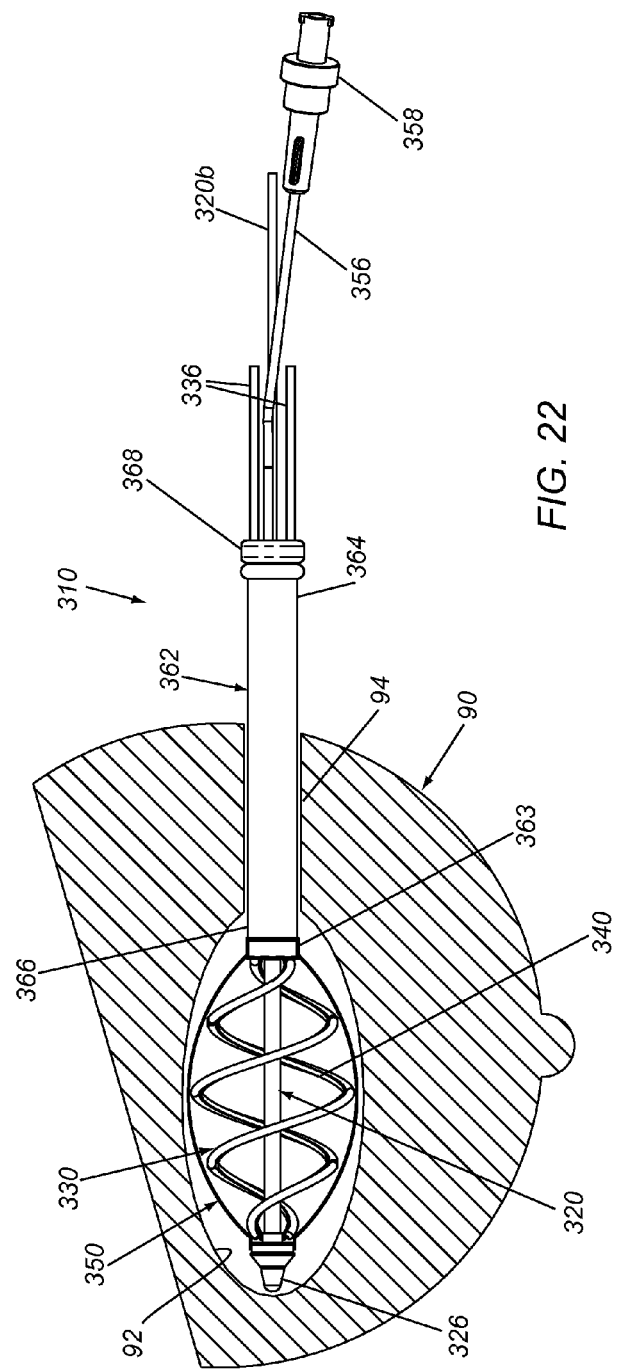

Turning to the drawings, FIGS. 1-4 show an exemplary embodiment of an expandable brachytherapy apparatus 10 that includes a proximal or tail portion 12, and a distal or therapy delivery portion 14, generally defining a longitudinal axis 16 extending therebetween. As described further below, the distal portion 14 may be deployed or introduced within a target location of a patient's body, e.g., a tumor or cavity within a breast or other body structure (not shown), and the proximal portion 12 may extend from the distal portion 14, e.g., such that the proximal portion 12 protrudes at least partially outside of the body structure. The distal portion 14 generally includes one or more helical members 30 that may be movable between a collapsed configuration, as shown in FIG. 4, e.g., for introduction through a tissue tract to a target location, and a fully deployed or expanded configuration, as shown in FIGS. 1-3, e.g., for providing a three dimensional array of pathways at the target location, as described further below.

In addition or alternatively, the apparatus 10 may be part of a system, e.g., including a tubular delivery device, such as an introducer sheath, catheter, cannula, trocar, obturator, and/or needle (not shown), for introducing the apparatus 10 into a target location, one more sources of radiation, and/or other components (also not shown), as described elsewhere herein and in the applications incorporated by reference elsewhere herein.

In the embodiment shown in FIGS. 1-4, the apparatus 10 includes an elongate core member 20 including a proximal end 22 and a distal end 24 terminating in a distal tip 25, a distal hub 26 coupled to the distal tip 25, and a proximal hub 60 movable relative to the core member 20. In addition, the apparatus 10 includes a plurality of flexible tubular members or other elongate members 30 that extend helically around the distal end 24 of the core member 20, e.g., between the proximal and distal hubs 60, 26.

For example, as shown, a pair of elongate members 30 are provided that include proximal ends 32 coupled to the proximal hub 60, distal ends 34 coupled to the distal hub 26, and expandable intermediate portions 35 that extend helically around the core member 20. As shown, the elongate members 30 may be offset radially from one another about the longitudinal axis 16, e.g., about one hundred eighty degrees (180°). The elongate members 30 extend helically around the core member 20 in the same helical direction, e.g., clockwise or counterclockwise around the core member 20, such that the elongate members 30 do not overlap or contact one another. This may minimize a profile of the apparatus 10 in the collapsed configuration, e.g., since the elongate members 30 may be wrapped closely around or contacting the core member 20 in the collapsed configuration without interfering with one another. It will be appreciated that, although two elongate members 30 are shown, additional elongate members 30 may be provided, e.g., three, four, or more (not shown), with the elongate members 30 offset radially relative to one another, e.g., distributed substantially evenly about the perimeter of the core member 20.

The distal hub 26 may be formed from one or more components integrally molded, machined, or otherwise formed together from a single piece, or as separate components that are attached together. The distal ends 34 of the elongate members 30 may be received within and/or otherwise secured to the distal hub 26, e.g., by bonding with adhesive, sonic welding, fusing, mating connectors, and the like. The distal hub 26 may provide a rounded and/or tapered distal tip for the apparatus 10, e.g., to facilitate substantially atraumatic introduction into a patient's body. Alternatively, the distal hub 26 may include a pointed or other sharpened distal tip (not shown) for facilitating advancing the apparatus 10 directly through tissue, e.g., by dissection or puncture of tissue between the patient's skin and a target location. Optionally, the distal hub 26 (and/or other components of the apparatus 10) may include radiopaque material, echogenic material, and the like to facilitate monitoring the distal hub 26 (and/or the apparatus 10) using external imaging, such as fluoroscopy, ultrasound, and the like.

The proximal hub 60 may be provided from one or more pieces, e.g., that may be slidably mounted around the core member 20 and coupled to the proximal ends 32 of the elongate members 30. For example, the proximal hub 60 may include an annular collar that includes nipples or passages (not shown) for receiving the proximal ends 32 of the elongate members 30 to substantially permanently attach the proximal ends 32 to the proximal hub 60, e.g., by interference fit. In addition or alternatively, the proximal ends 32 may be attached to the proximal hub 60 by bonding with adhesives, sonic welding, fusing, cooperating connectors, and the like. Alternatively, the proximal hub 60 may be formed from separate components (not shown) that may be attached together around the core member 20, e.g., using an interference fit, cooperating connectors, bonding using adhesive, sonic welding, and the like.

An actuator member 62 may extend proximally from the proximal hub 60 for controlling movement of the proximal hub 60 from the proximal portion 12 of the apparatus 10. For example, as shown, the actuator member 62 includes an elongate sleeve or tubular body including a proximal end 64 adjacent the proximal end 22 of the core member 20 and a distal end 66 coupled to the proximal hub 60. The sleeve 62 may be movably disposed around the core member 20 such that the sleeve 62 may be rotated and/or directed axially to move the proximal hub 60 to expand and/or collapse the elongate members 30, as described further below.

The elongate members 30 may be elongate, fixed length tubular members or "catheters," each including a proximal end 32, a distal end 34, and a lumen (not shown) extending therebetween, e.g., along the expandable intermediate portion 35 that extends helically around the core member 20. The proximal ends 32 may be received in, through, and/or otherwise coupled to the proximal hub 60, e.g., as described elsewhere herein.

As shown, the elongate members 30 may include individual catheter tubes 30 coupled to respective struts or other supports 40. For example, the supports 40 may be elongate wires, strips of material, and the like, e.g., made from metal, such as stainless steel or Nitinol, plastic, or composite material, that may be elastically deflected during use of the apparatus 10, e.g., when the distal portion 14 is directed between the collapsed and expanded configurations. Generally, the supports 40 include a circumferential or transverse "width" and a radial "thickness," e.g., having a rectangular or elliptical cross-section to cause preferential bending of the supports 40 radially outwardly into a substantially continuous helical shape. The supports 40 may have a substantially homogeneous cross-section along their lengths or may have varying cross-sections (not shown), e.g., if desired to vary the rigidity and/or bias of the elongate members 30 using the supports 40.

The supports 40 may extend at least partially along the intermediate portion 35 of the elongate members 30. For example, the proximal ends 42 of the supports 40 may be attached or secured to the proximal hub 60 and/or the proximal ends 32 of the elongate members 30, and the distal ends 44 may be attached or secured to distal hub 26 and/or the distal ends 34 of the elongate members 30. In an exemplary embodiment, the distal ends 44 may be integrally formed with a sleeve or collar (not shown) that may be received within, around, and/or otherwise secured to the distal hub 26, similar to the embodiments described in the applications incorporated by reference herein. In addition, the proximal ends 42 may include connectors (not shown) that may be interlocked with one another and/or the proximal hub 60. Alternatively, the proximal ends 42 may be integrally formed with a collar or sleeve (not shown), similar to the distal ends 44.

The supports 40 may be oriented such that their major dimension or width is disposed generally circumferentially relative to the core member 20 and their minor dimension or thickness is disposed generally radially. For example, the supports 40 may bias the elongate members 30 to extend along a substantially continuous helical path that tapers outwardly from the proximal and distal ends 32, 34 to a maximum diameter in the intermediate portions 35 in the expanded configuration, as can be seen in FIGS. 1 and 2. The supports 40 may be attached or otherwise secured to the elongate members 30 at one or more locations along their lengths, e.g., using shrink tubing, bonding with adhesive, sonic welding, and the like. For example, heat shrink tubing (not shown) may be provided at one or more locations along the length of the elongate members 30 between the proximal and distal ends 32, 34 to couple movement of the elongate members 30 to the supports 40, e.g., as disclosed in the applications incorporated by reference herein.

Alternatively, the supports 40 may be provided within an additional lumen (not shown) within the elongate members 30, similar to apparatus 3600 shown in FIGS. 23A-23J, and the embodiments disclosed in the applications incorporated by reference elsewhere herein. In a further alternative, the supports 40 may be eliminated. For example, the elongate members 30 themselves may be configured, e.g., may have asymmetrical cross-sections (not shown) providing a moment of inertia that biases the elongate members 30 to expand helically outwardly towards a predetermined helical shape. Optionally, the supports 40 may provide shielding, in addition to or instead of supporting the elongate members 30, also as disclosed in the applications incorporated by reference herein.

In an exemplary embodiment, the supports 40 may be biased to a helical shape corresponding to the expanded configuration, yet may be resiliently collapsed inwardly to contract the elongate members 30 to the collapsed configuration. Alternatively, the supports 40 may be biased to a helical shape corresponding to the collapsed configuration, yet may be resiliently expanded outwardly to expand the elongate members 30 to the expanded configuration. For example, the supports 40 may be heat treated or otherwise processed to bias the material to the desired helical shape. In addition, the elongate members 30 may be biased to a desired helical shape or the elongate members 30 may be substantially flexible such that they assume the shape to which the supports 40 are biased.

With continued reference to FIGS. 1-4, tubular extensions 36 may be coupled to the proximal hub 60 and/or coupled directly to the proximal ends 32 of the elongate members 30, e.g., extending proximally from the proximal hub 60 to at least partially define the proximal portion 12 of the apparatus 10. For example, the tubular extensions 36 may be received in passages or over nipples (not shown) on the proximal hub 60 similar to the proximal ends 32 of the elongate members 30 such that lumens of the tubular extensions 36 communicate with lumens of the respective elongate members 30. As shown, each tubular extension 36 includes an opening 36a providing access into a respective lumen, e.g., through the tubular extension 36 and into a respective elongate member 30, for receiving a radiation source, as described elsewhere herein. Alternatively, the tubular extensions 36 may be formed as an integral part of the elongate members 30, e.g., as a continuous extrusion, molding, and the like, such that the elongate members 30 extend continuously from the openings 33a to the distal ends 34.

The tubular extensions 36 may remain substantially free relative to one another or may be at least partially constrained relative to one another. For example, as shown, the tubular extensions 36 may be biased to extend substantially parallel to the longitudinal axis 16 along the core member 20 and then bend or turn outwardly away from the proximal end 22 of the core member 20 adjacent the openings 36a. Optionally, the tubular extensions 36 may pass through or be captured by a collar or other structure (not shown) on the proximal portion 12 of the apparatus, thereby keeping the tubular extensions 36 together, organized, and/or otherwise limiting relative movement of the tubular extensions 36, similar to embodiments in the applications incorporated by reference herein. For example, a collar may be provided that includes numbers or other indicia (not shown) to identify respective openings 36a during use.

Generally, the tubular extensions 36 may be flexible, e.g., to allow the tubular extensions 36 to be curved or otherwise bent individually and/or together. Thus, the proximal portion 12 of the apparatus 10 may be easily bent, e.g., to accommodate securing the proximal portion 12 to a patient, for example, to the patient's skin adjacent a tract communicating with a treatment site within which the distal portion 14 has been introduced. Optionally, the tubular extensions 36 may include one or more features, such as those disclosed in the applications incorporated by reference herein, to enhance flexibility and/or bending of the tubular extensions 36 to minimize a profile of the proximal portion 12 of the apparatus 10.

Similarly, the core member 20 may include one or more regions between the proximal and distal ends 22, 24 constructed from different materials and/or methods, e.g., to provide desired flexibility or rigidity for the proximal and distal portions 12, 14 of the apparatus 10. For example, the distal end 24 may include a substantially rigid tubular body, e.g., extending at least between the proximal and distal hubs 60, 26 to maintain the relative position of the proximal and distal hubs 60, 26 and/or provide sufficient support for the elongate members 30 as they are expanded and/or collapsed. The proximal end 22 may include one or more semi-rigid or substantially flexible tubular members, e.g., to allow the proximal end 22 to be bent, folded, or otherwise directed against a patient's skin, e.g., while the distal end 24 is positioned within a target region, as described elsewhere herein.

For example, the proximal end 22 of the core member 20 may include a detent tube 20a that extends through the sleeve 62 and is coupled to the tubular body of the distal end 24 of the core member 20. Thus, the detent tube 20a and the tubular extensions 36 may substantially define the proximal portion 12 of the apparatus 10, e.g., to provide flexibility to bend or otherwise minimize a profile of the proximal portion 12 during use. In addition or alternatively, a central catheter 20b may be provided that includes a lumen (not shown) for receiving a source of radiation (also not shown), similar to the elongate members 30. For example, the central catheter 20b may be a tubular body that extends into and through the detent tube 20a and through the distal end 24 of the core member 20 to the distal tip 25, e.g., to provide a substantially uniform diameter lumen for receiving a source of radiation.

In addition or alternatively, as shown in FIGS. 1 and 2, a stylet 80 may be inserted into the lumen of the central catheter 20b, e.g., to substantially seal and/or prevent material from entering the lumen. The stylet 80 may also enhance the rigidity of the central catheter 20b and/or detent tube 20a, e.g., to facilitate support and/or manipulation of the apparatus 10 during introduction. Optionally, stylets or other inserts (not shown) may also be provided in the lumens of the tubular extensions 36 and/or elongate members 30, e.g., similar to those disclosed in the applications incorporated by reference elsewhere herein.

With particular reference to FIG. 4, the apparatus 10 may be provided initially with the proximal hub 60 and actuator member 62 in a proximal or first position, i.e., with the proximal and distal hubs 60, 26 spaced furthest apart, thereby providing the elongate members 30 in the collapsed condition. As shown, the elongate members 30 and supports 40 may extend helically around and/or in contact with the core member 20. Alternatively, the apparatus 10 may be provided in the expanded configuration, e.g., after manufacturing, and may be directed to the collapsed configuration immediately before use.

Optionally, the apparatus 10 may include cooperating detents for releasably securing the actuator member 62 in the proximal position, thereby securing the elongate members 30 in the collapsed configuration. For example, the actuator member 62 may include a detent clip 68 attached on the proximal end 64 that may engage a proximal or first detent 23a on the detent tube 20a. The detent clip 68 includes a tubular clip body 68a that is slidably mounted around the detent tube 20a, a pair of detent elements 68b hingedly mounted to the clip body 68a, and a pair of arms 68c coupled to the detent elements 68b. Thus, the detent elements 68b may be directed away from the detent tube 20a by compressing the arms 68c, and may be biased to return inwardly, e.g., to engage the first detent 23a.

The first detent 23a may be an annular ring molded on or attached to the detent tube 20a at a predetermined location, e.g., corresponding to the actuator member 62 being in the proximal position and/or the elongate members 30 being in the collapsed configuration. Alternatively, the first detent 23a may include one or more individual tabs, e.g., a pair of tabs (not shown) spaced apart around the detent tube 20a at locations aligned axially with the detent elements 68b on the detent clip 68. The detent elements 68b may include opposing jaws or gripped elements including recesses for receiving a portion of the first detent 23a when the arms 68c are released, thereby preventing subsequent movement of the actuator member 62 relative to the detent tube 20a.

Similarly, a second or distal detent 23b may be provided on the detent tube 20a, e.g., distal to the first detent 23a, for securing the actuator member 62 in a distal or second position, thereby securing the elongate members 30 in the expanded configuration. The second detent 23b may have a profile such that the actuator member 62 may pass freely over the second detent 23b during axial movement of the actuator member 62. For example, similar to the first detent 23a, the second detent 23b may be an annular ring molded on or attached to the detent tube 20a at a predetermined location. Thus, the arms 23c may be activated to release the first detent 23a from the detent elements 23b and then the actuator member 62 may be advanced to expand the elongate members 30, e.g., until the detent elements 23b engage the second detent 23b.

Optionally, the second detent 23b may include a ramped proximal surface, e.g., such that the detent elements 23b may automatically slide over the second detent 23b when the actuator member 62 is advanced, and a blunt distal surface, e.g., such that proximal movement of the actuator member 62 is not possible without first activating the arms 23c to open the detent elements 23b. Similarly, the first detent 23a may include a ramped distal surface, e.g., such that the detent elements 23b may automatically slide over the first detent 23a when the actuator member 62 is retracted from the second position, and a blunt proximal surface, e.g., such that distal advancement of the actuator member 62 is not possible without first activating the arms 23c to open the detent elements 23b.

In addition or alternatively, other cooperating detents or features (not shown) may be provided on the actuator member 62 and/or detent tube 20a, e.g., to releasably secure the actuator member 62 in the first and/or second positions. For example, if the actuator member 62 is rotatable for at least partially expanding and/or collapsing the elongate members 30, the detent tube 20a may include a tab or other feature (not shown) extending outwardly from the detent tube 20a at a predetermined location that may be slidably receiving in a slot or other track (not shown) in the actuator member 62, thereby allowing the actuator member 62 to be rotated between first and second positions corresponding to the collapsed and expanded configurations of the elongate members 30.

Turning to FIGS. 5 and 6, the apparatus 10 may be used for brachytherapy treatment within a tissue structure, for example, within a breast 90. As shown, the breast 90 may have a cavity (e.g., a lumpectomy cavity 92) formed therein, e.g., by removal of cancerous tissue. If an introducer sheath is used (not shown), the introducer sheath may be introduced into the cavity 92, as described in the applications incorporated by reference herein. For example, a trocar (also not shown) may be provided in the introducer sheath that includes a sharpened distal end, and the introducer sheath and trocar may be advanced directly through tissue, thereby creating a tract 94 communicating with the cavity 92. Alternatively, the tract 94 may be created in advance, e.g., using a needle or other device (not shown). The trocar may then be removed, leaving the introducer sheath to provide a path through the tissue of the breast 90 into the cavity 92. Optionally, if desired, the inner surface of the introducer sheath may include lubricious material to facilitate introducing the apparatus 10 and/or other devices therethrough.

As shown in FIG. 5, the apparatus 10 may be inserted through the tract 94, e.g., through the introducer sheath (not shown), with the elongate members 30 in the collapsed configuration, e.g., until the distal hub 26 is disposed within the cavity 92. Alternatively, the apparatus 10 may be inserted directly through an existing incision without an introducer sheath, e.g., the incision used to perform the lumpectomy, or via a new incision created for delivering the apparatus 10. In a further alternative, the apparatus 10 may be advanced directly through tissue, e.g., if the distal hub 26 includes a sharpened tip (not shown), as described in the applications incorporated by reference herein.

In one embodiment, the apparatus 10 may be provided to the user with the elongate members 30 in the collapsed configuration. For example, the apparatus 10 may be manufactured with the elongate members 30 biased to the expanded configuration, e.g., by the supports 40, and the elongate members 30 may be collapsed to the collapsed configuration, e.g., before packaging and/or shipment. The detent clip 68 may be engaged with the first detent 23a to secure the apparatus 10 in the collapsed configuration. Alternatively, the apparatus 10 may be packaged and/or shipped with the elongate members 30 in the expanded configuration. Shortly before use, the actuator member 62 may be retracted to collapse the elongate members 30 to the collapsed configuration, e.g., being secured by the detent clip 68 engaging the first detent 23a. This alternative may be useful if the apparatus 10 may be stored for an extended time before use, e.g., to reduce the risk of the supports 40 losing some of their bias to the expanded configuration.

During insertion, the apparatus 10 may be positioned such that the distal hub 26 is placed in the far end of the cavity 92, as shown in FIG. 5, e.g., such that the elongate members 30 (in the collapsed configuration) extend partially from the cavity 92, e.g., into the tract 94. Once the apparatus 10 is positioned within the cavity 92, the introducer sheath (if used) may be removed from around the apparatus 10. For example, if the introducer sheath includes a longitudinal slit or is otherwise separable, the introducer sheath may be pulled transversely away from the apparatus 10, thereby causing side edges defining the slit to separate and pass around the apparatus 10 (not shown). As shown in FIG. 5, the apparatus 10 is shown with the introducer sheath (or other introducer device) completely removed, the distal portion 14 of the apparatus 10 positioned within the cavity 92, and the proximal portion 12 extending from the cavity 92, through the tract 94, and out of the breast 90. Thus, the apparatus 10 is ready for expansion and delivery of radiation.

Turning to FIG. 6, the actuator member 62 may be advanced distally to direct the proximal hub 60 distally relative to the distal hub 26, thereby causing the elongate members 30 to expand outwardly within the cavity 92. For example, the actuator member 62 may be advanced until the detent clip 68 engages a second detent 23b on the detent tube 20a, thereby securing the elongate members 30 in the expanded configuration. Optionally, the detent tube 20a may include multiple detents (not shown), e.g., such that the elongate members 30 may be expanded to multiple diameters or sizes, e.g., to accommodate different size cavities.

In addition or alternatively, the actuator member 62 may be rotatable relative to the core member 20 to at least partially expand the elongate members 30 towards the expanded configuration. For example, the actuator member 62 may be rotated before or after advancement, if desired, to adjust the size of the elongate members 30 in the expanded configuration. Alternatively, the actuator member 62 may only be rotatable (and not advanceable axially). For example, the supports 40 may be biased to expand the elongate members 30 to the expanded configuration. The actuator member 62 may be rotated to wind the elongate members 30 around the core member 20, thereby collapsing the elongate members 30 the collapsed configuration without axial movement. The actuator member 62 may then be rotated in the opposite direction to unwind the elongate members 30 from around the core member 20 and allow them to expand to the expanded configuration.

When the apparatus 10 is directed to the expanded configuration, the elongate members 30 may have sufficient bias to at least partially direct tissue surrounding the cavity outwardly and/or cause the tissue to invaginate between adjacent elongate members 30, as disclosed in the applications incorporated by reference herein. Optionally, the elongate members 30 and/or the distal portion 14 may include one or more extensions, membranes, balloons, or other features to shape the cavity 92 in a desired manner, e.g., as described elsewhere herein and/or in the applications incorporated by reference herein.

In addition or alternatively, the elongate members 30 may have sufficient bias to maintain a desired maximum axial spacing between adjacent windings of the elongate members 30. For example, as shown in FIG. 3, it may be desirable to have the axial spacing between adjacent windings be no more than about one and a half centimeters (1.5 cm) to facilitate dose planning and ensuring sufficient radiation is delivered to adjacent tissue. The axial spacing between adjacent windings may be substantially constant between the proximal and distal hubs 60, 26 or may vary, as desired.

Once the elongate members 30 are directed to the expanded configuration, one or more sources of radiation (not shown) may be directed into the elongate members 30, e.g., via the openings 36a and tubular extensions 36, and/or into the central catheter 20b. For example, the elongate members 30 may be sized and/or otherwise configured to receive commercially available HDR afterloader transfer tubes (not shown), such as those available from Varian and Nucletron.

In an exemplary procedure, an HDR source may be introduced into a first elongate member 30, advanced to a first position, and maintained at the first position for a predetermined time. The HDR source may then be advanced and/or retracted to a second position, and maintained there for a predetermined time, etc. The HDR source may then be removed from the first elongate member 30, and then introduced into the other elongate member 30 (or sequentially into each elongate member if the apparatus 10 includes more than two elongate members, not shown), in a similar manner.

Alternatively, a plurality of LDR sources may be delivered into the elongate members 30 and/or central catheter 20b, and remain indwelling for a predetermined time. For example, individual pods or other radiation sources may be loaded into respective elongate members 30 simultaneously or sequentially, thereby providing a three dimensional array of seeds or radiation sources that may remain in the target location for an extended period of time. The seeds may be spaced apart on each pod and/or may have different radioactive intensities, according to the dose plan.

In a further alternative, one or more radiation sources may be preloaded or secured within the elongate members 30 before introduction into the cavity. Thus, radiation may be delivered via the elongate members 30 and/or central catheter 20b according to a desired treatment plan, as described in the applications incorporated by reference herein.

Optionally, the apparatus 10 may be secured relative to the target tissue region to prevent subsequent migration. For example, tape, an external collar, and/or other features (not shown) may be used to secure the proximal portion 12 of the apparatus 10 extending from the breast 90, e.g., to the patient's skin. Alternatively, the elongate members 30 may sufficiently engage the tissue surrounding the cavity 92 in the expanded configuration to prevent substantial migration. If the apparatus 10 is to remain within the target tissue region for an extended period of time, the tubular extensions 36 and/or detent tube 20a may be folded or otherwise directed against the patient's skin where they exit the tract 94, e.g., between treatments, and taped or otherwise secured against the patient's skin. Alternatively, at least a portion of the proximal portion 12 of the apparatus 10 may be removable (not shown), e.g., to reduce the profile of the proximal portion 12 extending from the patient's body.

Upon completion of brachytherapy treatment, the actuator member 62 may be retracted to return the elongate members 30 back to the collapsed configuration, and the apparatus 10 may be removed from the breast 90 via the tract 94. For example, the actuator member 62 may be withdrawn proximally (e.g., after releasing the second detent 23b from the detent clip 68) until the detent clip 68 engages the first detent 23a. In addition or alternatively, the actuator member 62 may be rotated to at least partially collapse the elongate members 30, as described elsewhere herein.

Before treating the patient, it may be desirable to create a dose plan to determine the course of treatment. Dose planning may be accomplished using a variety of imaging methods (e.g., CT or ultrasound) and/or using dose planning software for either HDR or LDR applications. The timing and general scenario of the dose planning process is at the discretion of the clinical physicist/oncologist. However, one such scenario may include placing the apparatus 10 into the target tissue region and actuating the distal portion 14 into the expanded configuration. Then, with the aid of imaging (e.g., CT), both the target tissue region and the position of the elongate members 30 may be delineated. A dose plan may then be developed and, if desired, modified as configuration adjustments are made to the apparatus 10 and/or the elongate members 30.

The elongate members 30 and/or other components of the apparatus 10 may include markers to facilitate identifying the orientation of the apparatus 10 during dose planning, as described elsewhere herein.

Turning to FIGS. 7-10, another exemplary embodiment of an expandable brachytherapy apparatus 110 is shown that includes a proximal or tail portion 112 and a distal or therapy delivery portion 114, generally defining a longitudinal axis 116 extending therebetween. Similar to the previous embodiment, the apparatus 110 includes an elongate core member 120 including a proximal end 122 and a distal end 124 (and, optionally, including a detent tube 120a and central catheter 120b, similar to the previous embodiment), a distal hub 126 coupled to the distal end 124, and a proximal hub 160 movable relative to the core member 120. In addition, the apparatus 110 includes a pair of flexible tubular members, catheters, or other helical elongate members 130 that extend helically around the distal end 124 of the core member 120, e.g., between the proximal and distal hubs 160, 126, also similar to the previous embodiment.

An actuator member 162 may be coupled to the proximal hub 160 for controlling movement of the proximal hub 160 from the proximal portion 112 of the apparatus 110. For example, similar to the previous embodiment, the actuator member 162 may include an elongate sleeve or tubular body including a proximal end 164 adjacent the proximal end 122 of the core member 120 and a distal end 166 coupled to the proximal hub 160. The sleeve 162 may be movably disposed around the core member 120 such that the sleeve 162 may be rotated and/or directed axially to move the proximal hub 160 to expand and/or collapse the elongate members 130, as described elsewhere herein.

The elongate members 130 each includes a proximal end 132, a distal end 134, and a lumen (not shown) extending therebetween, e.g., along an expandable intermediate portion 135 that extends helically around the core member 120. The proximal ends 132 may be received in, through, and/or otherwise coupled to the proximal hub 160, e.g., as described elsewhere herein. Also similar to the previous embodiment, the elongate members 130 may include individual catheter tubes 130 coupled to supports 140, and tubular extensions 136 may be coupled to the proximal hub 160 and/or coupled directly to the proximal ends 132 of the elongate members 130, e.g., extending proximally from the proximal hub 160. As shown, each tubular extension 136 includes an opening 136a providing access into a respective lumen, e.g., through the tubular extension 136 and into a respective elongate member 130, for receiving a radiation source, as described elsewhere herein.

The core member 120 may include one or more regions between the proximal and distal ends 122, 124 constructed from different materials and/or methods, e.g., to provide desired flexibility or rigidity for the proximal and distal portions 112, 114 of the apparatus 110, similar to the previous embodiment. For example, the distal end 124 may include a substantially rigid tubular body, e.g., extending at least between the proximal and distal hubs 160, 126, and the proximal end 122 of the core member 120 may include a detent tube 120a that extends through the sleeve 162 and a central catheter 120b.

Unlike the previous embodiment, the apparatus 110 also includes a balloon or other expandable member 150 on the distal portion 114, extending at least partially between the proximal and distal hubs 160, 126. As shown, the balloon 150 may be disposed between the elongate members 130 and the core member 120, e.g., such that the elongate members 130 extend along or around an outer surface of the balloon 150. Alternatively, the balloon 150 may be disposed around the elongate members 130 (not shown), similar to other embodiments herein.

As best seen in FIG. 9, the balloon 150 includes a distal end 154 coupled to the core member 120, e.g., immediately adjacent the distal hub 126 (or alternatively coupled directly to the distal hub 126), and a proximal end 152 coupled to the core member 120 at a predetermined distance proximal to the distal end 154. For example, the proximal end 152 of the balloon 150 may be attached at a predetermined location on the core member 120 such that the proximal end 152 is disposed adjacent the proximal hub 160 and/or the proximal ends 132 of the elongate members 130 when the proximal hub 160 is advanced to direct the elongate members 130 to the expanded configuration, as best seen in FIG. 8. Alternatively, if the balloon 150 is formed from elastic material, the proximal end 152 of the balloon 150 may be attached or otherwise coupled to the proximal hub 160 (not shown), e.g., such that the length of the balloon 150 changes as the proximal hub 160 is directed axially along the core member 120.

The proximal and distal ends 152, 154 of the balloon 150 may be attached to the core member 120 (or other component of the apparatus 110), e.g., by bonding with adhesive, sonic welding, fusing, overlying bands or collars, and the like. Thus, the proximal and distal ends 152, 154 may provide a substantially fluid tight seal to allow inflation media to be introduced into an interior of the balloon 150, i.e., between the balloon wall and the core member 120, to expand the balloon 150. The balloon 150 may be formed from substantially flexible or compliant material, e.g., such that the size of the balloon 150 is proportional to the amount of inflation media introduced into the interior of the balloon 150. Alternatively, the balloon 150 may be formed from non-compliant material, e.g., such that the balloon 150 may be expanded to a predetermined size and/or shape once sufficient fluid is introduced into the interior of the balloon 150 without expanding further (until a rupture pressure is achieved within the balloon interior).

The core member 120 may include an inflation lumen (not shown) that extends between the proximal and distal ends 122, 124 thereof and communicates with the interior of the balloon 150 for delivering inflation media into and/or evacuating inflation media from within the interior of the balloon 150. For example, with additional reference to FIGS. 9 and 10, a balloon port 156 may be provided on the proximal end 122 of the core member 120 that includes a luer valve or other connector 158. A syringe 159 or other source of inflation media and/or vacuum may be coupled to the connector 158, e.g., for delivering or evacuating saline, air, nitrogen, or other inflation media into/from the inflation lumen via the connector 158 and port 156, i.e., for inflating or collapsing the balloon 150, as described further below.

As can be seen in FIGS. 7, 8, and 10, the elongate members 130 may be expandable independently of the balloon 150. For example, the actuator member 162 may be advanced distally to direct the elongate members 130 from the collapsed configuration to the expanded configuration, as shown. Similar to the previous embodiment, the actuator member 162 may include a detent clip 168 or other element that may engage one or more detents 123 on the proximal end 122 of the core member 120, e.g., a first detent 123a for securing the elongate members 130 in the collapsed configuration, as shown in FIGS. 9 and 9A, and a second detent 123b for securing the elongate members 130 in the expanded configuration, as shown in FIGS. 10 and 10A.

Once the elongate members 130 are directed to the expanded configuration and the actuator member 162 is secured in the distal position, the balloon 150 may be inflated by introducing inflation media into its interior. When fully inflated, the balloon 150 may be spaced apart inwardly from at least a portion of the elongate members 130, as shown in FIGS. 7, 8, and 10. Alternatively, the balloon 150 may be expanded until it contacts the elongate members 130, e.g., to press surrounding tissue outwardly, as described further below. Alternatively, the balloon 150 may be attached or otherwise coupled to the elongate members 130 (not shown), e.g., such that the balloon 150 expands at least partially as the elongate members 130 are directed to the expanded configuration. If additional expansion of the balloon 150 is desired, the balloon 150 may then be inflated by directing inflation media into the interior of the balloon 150. In a further alternative, the balloon 150 may simply be a membrane attached to the elongate members 130 (not shown), and the inflation lumen, port 156, and valve 158 may be eliminated.

Turning to FIGS. 11 and 12, the apparatus 110 may be used for brachytherapy treatment within a tissue structure, for example, within a breast 90 including a lumpectomy cavity 92 formed therein, e.g., by removal of cancerous tissue. As shown in FIG. 11, the apparatus 110 may be inserted through tract 94, e.g., through an introducer sheath (not shown) or directly through tissue, with the elongate members 130 in the collapsed configuration and the balloon 150 deflated, e.g., until the distal hub 126 is disposed within the cavity 92.

In one embodiment, the apparatus 110 may be provided to the user with the elongate members 130 in the collapsed configuration and the balloon 150 deflated. Alternatively, the apparatus 110 may be packaged and/or shipped with the elongate members 130 in the expanded configuration, similar to the previous embodiment, but with the balloon 150 deflated. Shortly before use, the actuator member 162 may be retracted to collapse the elongate members 130 to the collapsed configuration, and, optionally, secured by engaging the detent clip 168 with the first detent 123a.

During insertion, the apparatus 110 may be positioned such that the distal hub 126 is placed in the far end of the cavity 92, as shown in FIG. 11, e.g., such that the elongate members 130 (in the collapsed configuration) extend partially from the cavity 92, e.g., into the tract 94. In this position, the balloon 150 may be disposed entirely within the cavity 92, as shown, or may also extend from the cavity 92, e.g., if the proximal end 152 of the balloon 150 is coupled to the proximal hub 160.

Turning to FIG. 12, the actuator member 162 may be advanced distally to direct the proximal hub 160 distally relative to the distal hub 126, thereby causing the elongate members 130 to expand outwardly within the cavity 92. For example, the actuator member 162 may be advanced until the detent clip 168 engages the second detent 123b on the detent tube 120a, thereby securing the elongate members 130 in the expanded configuration, similar to the previous embodiment. In addition or alternatively, the actuator member 162 may be rotated relative to the core member 120 to at least partially expand the elongate members 130 towards the expanded configuration, similar to other embodiments herein. For example, the actuator member 162 may be rotated before or after advancement, if desired, to adjust the size of the elongate members 130 in the expanded configuration, e.g., to press the elongate members 130 outwardly against tissue surrounding the cavity 92, similar to other embodiments herein. When the apparatus 110 is directed to the expanded configuration, the elongate members 130 may have sufficient bias to at least partially direct tissue surrounding the cavity outwardly and/or cause the tissue to invaginate between adjacent elongate members 130.

Once the elongate members 130 are directed to the expanded configuration, the balloon 150 may be inflated, e.g., by coupling syringe 159 to the connector 158 and introducing inflation media into the interior of the balloon 150. The balloon 150 may be inflated until the balloon 150 presses against or otherwise contacts the elongate members 130 and/or surrounding tissue. For example, the balloon 150 may be expanded sufficiently to further shape the cavity 92 and/or surrounding tissue in addition to any shaping achieved with the elongate members 130 alone. Alternatively, the balloon 150 may be inflated until it is spaced slightly away from the elongate members 130, e.g., simply to prevent excess tissue from invaginating between the elongate members 130.

One or more sources of radiation (not shown) may then be directed into the elongate members 130, e.g., via openings 136a and tubular extensions 136, and/or into the central catheter 120b, similar to the other embodiments herein. For example, an HDR source may be introduced into a first elongate member 130, advanced to a first position, and maintained at the first position for a predetermined time. The HDR source may then be advanced and/or retracted to a second position, and maintained there for a predetermined time, etc. The HDR source may then be removed from the first elongate member 130, and then introduced into the other elongate member 130 in a similar manner.

Optionally, the apparatus 110 may be secured relative to the target tissue region to prevent subsequent migration. Alternatively, the elongate members 130 may sufficiently engage the tissue surrounding the cavity 92 in the expanded configuration to prevent substantial migration. For example, if the apparatus 110 is to remain within the target tissue region for an extended period of time, the tubular extensions 136 and/or detent tube 120a may be folded or otherwise directed against the patient's skin where they exit the tract 94, e.g., similar to the other embodiments herein.

Upon completion of brachytherapy treatment, the balloon 150 may be deflated, e.g., by coupling syringe 159 or another source of vacuum to the connector 158 and evacuating the inflation media from the interior of the balloon 150. The actuator member 162 may then be retracted (e.g., after releasing the second detent 123b from the detent clip 168) to direct the elongate members 130 back towards the collapsed configuration, e.g., until the detent clip 168 engages the first detent 123a. In addition or alternatively, the actuator member 162 may be rotated to at least partially collapse the elongate members 130, as described elsewhere herein. The apparatus 110 may then be removed from the cavity 92 and the patient's body, similar to other embodiments herein.

Turning to FIGS. 13A-14B, yet another exemplary embodiment of an expandable brachytherapy apparatus 210 is shown that includes a proximal or tail portion 212 and a distal or therapy delivery portion 214, generally defining a longitudinal axis 216 extending therebetween. Similar to the previous embodiments, the apparatus 210 includes an elongate core member 220 including a proximal end 222 and a distal end 224, a distal hub 226 coupled to the distal end 224, and a proximal hub 260 movable relative to the core member 220. Optionally, if desired, the apparatus 210 may include a balloon or other expandable member (not shown) on the distal portion 214, similar to any of the other embodiments described elsewhere herein.

Unlike the previous embodiments, the apparatus 210 includes only a single flexible tubular member, catheter, or other helical elongate member 230 that extends helically around the distal end 224 of the core member 220, e.g., between the proximal and distal hubs 260, 226. Also unlike the previous embodiments, the elongate member 230 may be directed between collapsed and expanded configurations simply by rotation, rather than axial displacement, as described further below. FIGS. 17A and 17B show a similar alternative embodiment of an apparatus 210' that includes two elongate members 230' but otherwise includes similar features (labeled similarly other than adding a "'") and may be operated similar to the apparatus 210 of FIGS. 13A-14B.

As shown in FIGS. 13A and 13B, the elongate member 230 includes a proximal end 232 coupled to the proximal hub 260, a distal end 234 coupled to the distal hub 226, and a lumen (not shown) extending therebetween, e.g., along an expandable intermediate portion 235 that extends helically around the core member 220. The elongate member 230 may include a catheter tube coupled to a support 240, and a tubular extension 236 may be coupled to the proximal hub 260 and/or coupled directly to the proximal end 232 of the elongate member 130.

An actuator member 262 may be coupled to the proximal hub 260 for limiting or otherwise controlling movement of the proximal hub 260 from the proximal portion 212 of the apparatus 210. For example, similar to the previous embodiments, the actuator member 262 may include an elongate sleeve or tubular body including a proximal end 264 adjacent the proximal end 222 of the core member 220 and a distal end 266 coupled to the proximal hub 260. The sleeve 262 and core member 220 may be movable relative to one another such that one of the sleeve 262 and the core member 220 may be rotated relative to the other to expand and/or collapse the elongate members 230, as described elsewhere herein.

Unlike the previous embodiment, the apparatus 210 also includes an expansion handle 223 on the proximal end 222 of the core member 220, e.g., for controlling movement of the distal end 224 of the core member 220 relative to the actuator member 262 from the proximal portion 212 of the apparatus 210. For example, as shown in FIGS. 13B and 14B, the apparatus 210 may be provided with the elongate member 230 in the expanded configuration. Before use, the expansion handle 223 may be rotated in a first direction relative to the actuator member 262 to rotate the distal end 224 of the core member 220, and thereby wind the elongate member 230 around the core member 220 towards the collapsed configuration, as shown in FIGS. 13A and 14A.

Optionally, the apparatus 210 may include cooperating detents or elements for releasably securing the apparatus 210 with the elongate member 230 in the collapsed and/or expanded configuration. For example, as shown, the actuator member 262 may include an expansion lock 268 for releasably engaging the expansion handle 223 in first and/or second positions, corresponding to the collapsed and expanded configurations, respectively. As best seen in FIG. 14C, the expansion handle 223 may include a tab or other detent 223b that may be received in or otherwise engage a corresponding recess or cooperating detent 268b on the expansion lock 268. Thus, when the expansion handle 223 is rotated relative to the expansion lock 268 to expand the elongate member 230, the tab 223b may be free to slide relative to the expansion lock 268 until it is received in the recess 268b, thereby securing the elongate member 230 in the expanded configuration. Similarly, the expansion lock 268 may include another recess (not shown) for receiving the tab 223b (or a separate tab, not shown) when the expansion handle 223 is rotated in the opposite direction to direct the elongate member 230 to the collapsed configuration.

Turning to FIGS. 15 and 16, the apparatus 210 may be used for brachytherapy treatment within a tissue structure, e.g., within a breast 90 including a lumpectomy cavity 92, similar to the previous embodiments. As shown in FIG. 15, the apparatus 210 may be inserted through tract 94 with the elongate member 230 in the collapsed configuration, e.g., until the distal hub 226 is disposed within the cavity 92. During insertion, the apparatus 210 may be positioned such that the distal hub 226 is placed in the far end of the cavity 92, e.g., such that the elongate member 230 (in the collapsed configuration) is positioned entirely within the cavity 92, as shown.

As described above, the apparatus 210 may be provided to the user with the elongate member 230 in the collapsed configuration. Alternatively, the apparatus 210 may be provided with the elongate member 230 in the expanded configuration, and shortly before use, the expansion handle 223 may be rotated relative to the actuator member 262 to collapse the elongate member 230 to the collapsed configuration. The support 240 may elastically store potential energy, similar to a spring, when the elongate member 230 is wound around the core member 220, e.g., to bias the elongate member 230 to unwind and expand radially outwardly when released from the collapsed configuration. Alternatively, the support 240 may be biased towards the collapsed configuration, yet may be elastically expanded to direct the elongate member 230 to the expanded configuration by unwinding the support 240 and elongate member 230 partially from around the core member 220. Thus, in either case, the elongate member 230 may include additional windings around the core member 230 in the collapsed configuration than in the expanded configuration.

Turning to FIG. 16, once the apparatus 210 is properly positioned, the expansion handle 223 may be rotated relative to the actuator member 262 to rotate the core member 220 and distal hub 226 relative to the proximal hub 260, thereby causing the elongate member 230 to unwind and expand outwardly within the cavity 92. As shown in FIG. 14C, the expansion handle 223 may be rotated until the detent clip 223b is received in the recess 268b, thereby securing the elongate member 230 in the expanded configuration, similar to the previous embodiment.

For example, the expansion handle 223 may be rotated while the actuator member 262 is maintained substantially stationary. Alternatively, the actuator member 262 may be rotated while the expansion handle 223 is maintained substantially stationary, e.g., in the opposite direction, to achieve the same result. However, it may be easier to rotate the expansion handle 223 while maintaining the actuator member 262 substantially stationary, e.g., to avoid movement of the tubular extension 236 (e.g., which could otherwise wind around the central catheter 220b or other components outside the patient's body). This may be particularly true if two (or more) elongate members are provided as in the apparatus 210' of FIGS. 17A and 17B.

Once the elongate member 230 is directed sufficiently outward to the expanded configuration, one or more sources of radiation (not shown) may then be directed into the elongate member 230, e.g., via opening 236a and tubular extensions 236, and/or into the central catheter 220b, similar to the other embodiments herein. Optionally, the apparatus 210 may be secured relative to the target tissue region to prevent subsequent migration, e.g., similar to the other embodiments herein. Upon completion of brachytherapy treatment, the elongate member 230 may be directed back towards the collapsed configuration, e.g., by rotating the expansion handle 223 in the opposite direction (e.g., after releasing the detent 268b from the recess 223b). The apparatus 210 may then be removed from the cavity 92 and the patient's body, similar to other embodiments herein.

Turning to FIGS. 18-19, another exemplary embodiment of an expandable brachytherapy apparatus 310 is shown that generally includes a proximal or tail portion 312 and a distal or therapy delivery portion 314 defining a longitudinal axis 316 therebetween. Similar to the previous embodiments, the apparatus 310 includes an elongate core member 320 including a proximal end 322 and a distal end 324 (and, optionally, including a central catheter 320b, similar to the previous embodiments), a distal hub 326 coupled to the distal end 324, and a proximal hub 360 movable relative to the core member 320.

In addition, the apparatus 310 includes a pair of flexible tubular members, catheters, or other helical elongate members 330 that extend helically around the distal end 324 of the core member 320, e.g., between the proximal and distal hubs 360, 326, also similar to previous embodiments. The elongate members 330 each includes a proximal end 332, a distal end 334, and a lumen (not shown) extending therebetween. The proximal ends 332 may be received in, through, and/or otherwise coupled to the proximal hub 360, and the distal ends 334 may be received in and/or otherwise coupled to the distal hub 326. Also similar to the previous embodiments, the elongate members 330 may include individual catheter tubes coupled to supports 340, and tubular extensions 336 may be coupled to the proximal hub 360 and/or coupled directly to the proximal ends 332 of the elongate members 330, e.g., extending proximally from the proximal hub 360. As shown, each tubular extension 336 includes an opening 336a providing access into a respective lumen, e.g., through the tubular extension 336 and into a respective elongate member 330, for receiving a radiation source, as described elsewhere herein.

Unlike the previous embodiment, the apparatus 310 also includes a balloon or other expandable member 350 on the distal portion 314 that surrounds at least a portion of the core member 320 and the elongate members 330. As best seen in FIGS. 18 and 19, the balloon 350 includes a proximal end 352 coupled to a balloon hub 363 and a distal end 354 coupled to the distal hub 326. The balloon hub 363 may be substantially fixed relative to the core member 320, e.g., such that the distance between the balloon hub 363 and distal hub 326 and the length of the balloon 350 remains substantially constant during use of the apparatus 310. For example, one or more struts (not shown) may extend inwardly from the balloon hub 363 or outer sleeve 362 to the core member 320, e.g., between the proximal hub 360 and the proximal end 364 of the outer sleeve 362 such that the strut(s) do not interfere with movement of the elongate members 330 during advancement and/or retraction. Alternatively, if the balloon 350 is formed from elastic material, the proximal end 352 of the balloon 350 may be attached or otherwise coupled to the proximal hub 360 (not shown), e.g., such that the length of the balloon 350 changes as the proximal hub 360 is directed axially along the core member 320, and the balloon hub 363 may be eliminated.

The proximal and distal ends 352, 354 of the balloon 350 may be attached to the balloon hub 373 and distal hub 326, e.g., by bonding with adhesive, sonic welding, fusing, overlying bands or collars, and the like. Thus, the proximal and distal ends 352, 354 may provide a substantially fluid tight seal to allow inflation media to be introduced into an interior 351 of the balloon 350 to expand the balloon 350. The balloon 350 may be formed from substantially flexible or compliant material, e.g., such that the size of the balloon 350 is proportional to the amount of inflation media introduced into the interior 351 of the balloon 350, or the balloon 350 may be formed from non-compliant material, e.g., such that the balloon 350 may be expanded to a predetermined size and/or shape, similar to other embodiments herein.

The core member 320 may include an inflation lumen that extends between the proximal and distal ends 322, 324 of the core member 320 and communicates with the interior 351 of the balloon 350 for delivering inflation media into and/or evacuating inflation media from the interior 351 of the balloon 350. For example, the core member 320 may include an inflation tube 356 that extends from the balloon hub 363 to the proximal end 322 of the core member 320 and terminates in a luer valve or other connector 358. A syringe 359 or other source of inflation media and/or vacuum may be coupled to the connector 358, e.g., for delivering or evacuating inflation media via the connector 358 through the inflation tube 356 and balloon hub 363 into the interior 351 of the balloon 350, i.e., for inflating or collapsing the balloon 150, as described further below.

In addition, the apparatus 310 includes an outer sleeve 362 that is coupled to and extends proximally from the balloon hub 363. Thus, the inflation tube 356 and central catheter 320b (if included) may extend axially through the outer sleeve 362, e.g., from the balloon hub 363 to the proximal portion 312 of the apparatus 310. The outer sleeve 362 may include a proximal end 364 adjacent the distal end 322, and a distal end 366 attached to or otherwise coupled to the balloon hub 363. Thus, the outer sleeve 362, inflation tube 356, and central catheter 320b may remain substantially stationary relative to the balloon hub 363 and consequently relative to the distal end 324 of the core member 320 and the distal hub 326.

For example, the distal end 324 of the core member 320, e.g., between the balloon hub 363 and the distal hub 326, may be substantially rigid, while the inflation tube 356 and the central catheter 320b may be substantially flexible, e.g., similar to other embodiments herein. The outer sleeve 362 may also be substantially rigid, e.g., to support the distal portion 314 of the apparatus 310 from the proximal portion 312 extending from a patient's body (not shown).

The outer sleeve 362 may accommodate slidably receiving the proximal hub 360 therein, e.g., such that the proximal hub 360 may be directed axially relative to the balloon hub 363 and consequently the distal hub 326 for directing the elongate members 330 between the collapsed and expanded configurations.

For example, a tube plunger 368 may be provided on the proximal portion 312 of the apparatus 310 that is coupled to the tubular extensions 336 and/or to the proximal hub 360, e.g., by one or more longitudinal supports (not shown). Thus, the plunger tube 368 may provide an actuator member for controlling movement of the proximal hub 360 from the proximal portion 312 of the apparatus 310, e.g., to expand and/or collapse the elongate members 330.

As shown in FIGS. 18 and 18A, in the collapsed configuration, the elongate members 330 may extend from the distal hub 326 (shown in FIG. 18) through the balloon hub 363 and partially into the outer sleeve 362 (best seen in FIG. 18A). To direct the elongate members 330 to the expanded configuration, the tube plunger 368 may be advanced distally, thereby advancing the proximal hub 360, e.g., until the proximal hub 360 is aligned axially with the balloon hub 363. For example, the proximal hub 360 may be sized to slide concentrically into the balloon hub 363 when the elongate members 330 are fully deployed to the expanded configuration, as best seen in FIG. 19A. As can be seen in FIG. 19, in the expanded configuration, the elongate members 330 may be located between the balloon hub 363 and the distal hub 326, e.g., entirely within the interior 351 of the balloon 350.

The elongate members 330 may be expandable independently of the balloon 350. For example, the balloon 350 may be inflated before expanding the elongate members 330, and then the tube plunger 368 may be advanced to expand the elongate members 330. In the expanded configuration, the elongate members 330 may be spaced inwardly from the fully inflated balloon 350 or may contact the balloon 350. Alternatively, the elongate members 330 may be expanded before (or even instead of) inflating the balloon 350. For example, the balloon 350 may simply expand elastically as the elongate members 330 expand radially outwardly. Thereafter, if desired, the balloon 350 may be inflated further, as described further below.

When the elongate members 330 are directed to the expanded configuration, the elongate members 330 may be releasably secured in the expanded configuration. For example, the tube plunger 368 may include one or more detents or other elements (not shown) that may engage cooperating elements on the proximal end 364 of the outer sleeve 362. In addition or alternatively, the proximal hub 360 and/or balloon hub 363 may include cooperating detents or other features that releasably engage to secure the proximal hub 360 relative to the balloon hub 363. Similarly, cooperating elements may be provided for releasably securing the tube plunger 368 in the proximal position to secure the elongate members 330 in the collapsed configuration. For example, the proximal hub 360 and the inner surface of the outer sleeve 362 may include cooperating detents that engage when the tube plunger 368 is retracted sufficiently to direct the elongate members 330 to the collapsed configuration.

Turning to FIGS. 20-22, the apparatus 310 may be used for brachytherapy treatment within a tissue structure, for example, within a breast 90 including a lumpectomy cavity 92 accessed via a tract 94, similar to the previous embodiments. As shown in FIG. 20, the apparatus 310 may be inserted through tract 94 with the elongate members 330 in the collapsed configuration and the balloon 350 deflated, e.g., until the distal hub 326 is disposed within the cavity 92. Upon insertion, the apparatus 310 may be positioned such that the balloon hub 363 and distal hub 326 are located within the cavity 92, and the elongate members 330 (in the collapsed configuration) extend partially from the cavity 92 within the outer sleeve 362, e.g., into the tract 94. In this position, the balloon 350 may be disposed entirely within the cavity 92, as shown.

Once properly positioned, the balloon 350 may be inflated to contact tissue surrounding the cavity 92, e.g., by coupling a syringe 359 to the connector 358 and delivering inflation media from the syringe 359 through the inflation tube 356 into the interior 351 of the balloon 350. For example, the balloon 350 may be inflated to dilate and/or otherwise shape the cavity and the surrounding tissue. Thereafter, the tube plunger 368 may be advanced distally to direct the proximal hub 360 (not shown in FIG. 12, see FIG. 19A) distally relative to the distal hub 326, thereby causing the elongate members 330 to expand outwardly within the cavity 92, as shown in FIG. 21. For example, the tube plunger 368 may be advanced until cooperating detents on the tube plunger 368 and proximal end 364 of the outer sleeve 362 engage and/or until the proximal hub 360 is disposed adjacent the balloon hub 363 (best seen in FIG. 19A). Optionally, the tube plunger 368 may be rotatable relative to the core member 320 and/or outer sleeve 362 to at least partially expand the elongate members 330 towards the expanded configuration, similar to other embodiments herein.

Once the elongate members 330 are directed to the expanded configuration, the elongate members 330 may be spaced inwardly from the balloon 350 or the elongate members 330 may contact the balloon 350. Alternatively, the elongate members 330 may be directed to the expanded configuration without first inflating the balloon 350, such that the elongate members 330 at least partially expand the balloon 350 outwardly. Once expanded, the balloon 350 may be inflated, if desired, e.g., until the balloon 350 presses against or otherwise contacts the surrounding tissue.

One or more sources of radiation (not shown) may then be directed into the elongate members 330, e.g., via openings 336a and tubular extensions 336, and/or into the central catheter 320b, similar to the other embodiments herein. For example, an HDR source may be introduced into a first elongate member 330, advanced to a first position, and maintained at the first position for a predetermined time. The HDR source may then be advanced and/or retracted to a second position, and maintained there for a predetermined time, etc. The HDR source may then be removed from the first elongate member 330, and then introduced into the other elongate member 330 in a similar manner.

Optionally, the apparatus 310 may be secured relative to the target tissue region to prevent subsequent migration. Alternatively, the elongate members 330 may sufficiently engage the tissue surrounding the cavity 92 in the expanded configuration to prevent substantial migration. For example, if the apparatus 310 is to remain within the target tissue region for an extended period of time, the tubular extensions 336, inflation tube 356, and/or central catheter 320 may be folded or otherwise directed against the patient's skin where they exit the tract 94, e.g., similar to the other embodiments herein.

Upon completion of brachytherapy treatment, the balloon 350 may be deflated, e.g., by coupling syringe 359 or another source of vacuum to the connector 358 and evacuating the inflation media from the interior 351 of the balloon 350. Before or after deflating the balloon 350, the tube plunger 368 may be retracted (e.g., after releasing any cooperating detents, not shown) to direct the elongate members 330 back towards the collapsed configuration. The apparatus 310 may then be removed from the cavity 92 and the patient's body, similar to other embodiments herein.

Turning to FIGS. 23A-23G, another embodiment of an intracavitary brachytherapy apparatus 3600 is shown that includes a brachytherapy device 3602 having a distal or therapy delivery portion 3604 and a proximal or tail portion 3606.

Figure 23A:
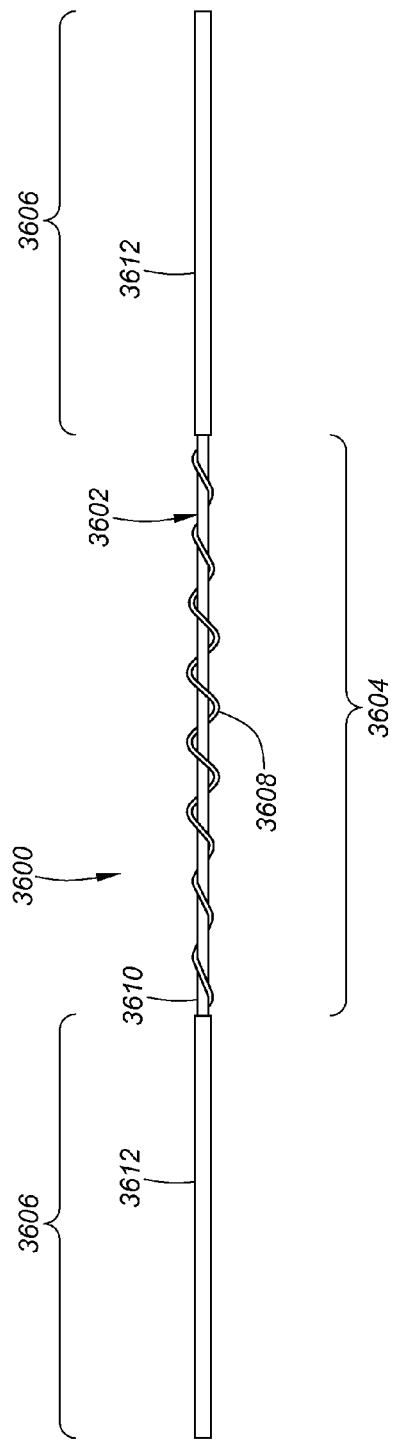
FIG. 23A is a side view of a sixth exemplary embodiment of a brachytherapy apparatus including an expandable therapy delivery portion that includes a helical catheter member in a collapsed configuration.
Figure 23B:
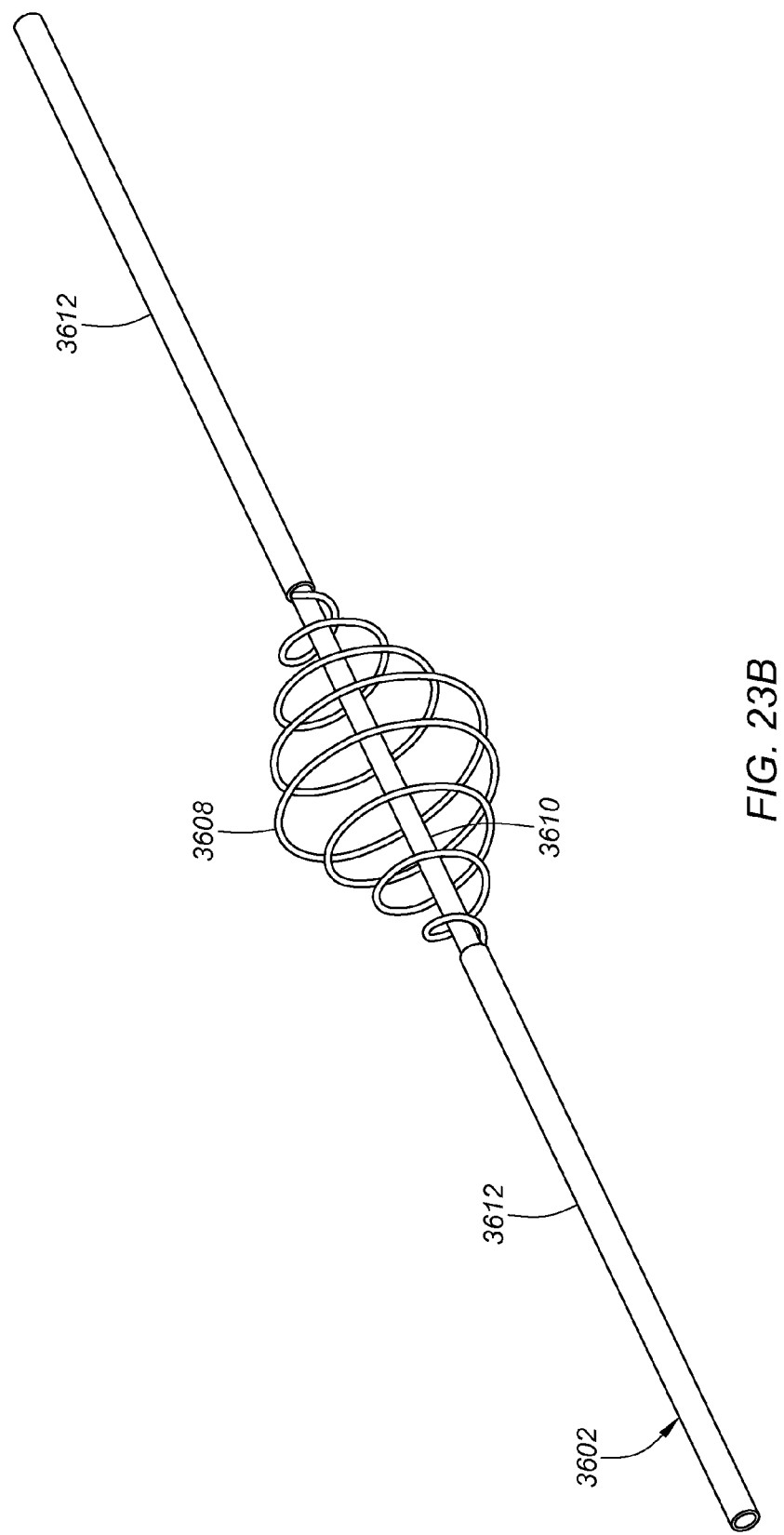

As FIG. 23A illustrates, the therapy delivery portion 3604 may be formed by a deformable and elongate radioactive source, e.g., coil member 3608. The coil member 3608 may form a helical coil wound about an elongate core member 3610. At least one end of the coil member 3608 (e.g., a proximal end) may be secured to an attachment member (e.g., a sleeve 3612) that translates and/or rotates about the core member 3610. This configuration provides a low profile device that may be inserted into a target region, e.g., lumpectomy cavity (not shown), via a relatively small incision. Once in place, the coil member 3608 may be deployed to form a spiral pathway within the cavity as shown in FIG. 23B. To deploy the device 3602, the sleeves 3612, which may extend outside of the body after implantation, may be rotated about the core member 3608 relative to one another. Relative rotation of the sleeves in one direction may cause the coil member 3608 to expand, i.e., move away, from the central core member 3610 towards the expanded configuration. Relative rotation of the sleeves 3612 in the opposite direction may similarly cause the coil member 3608 to contract around the core member 3610 back towards the collapsed configuration. The greater the expansile rotation, the more radial force may be exerted against the walls of the lumpectomy cavity. Greater force exerted against the walls of the lumpectomy cavity may result in a higher degree of invagination of the breast tissue within the turns of the expanded coil member 3608.

In addition to rotational movement of the sleeves 3612, the sleeves may also translate axially relative to the core member 3610. Axial translation permits adjustment in length of the coil member 3608 when in its expanded configuration. Due to the ability to independently control the axial length and the diameter (and hence the expansile force against the cavity walls) of the coil member 3608, the apparatus 3600 may be utilized to treat a variety of sizes and shapes of lumpectomy cavities.

FIG. 23C is an enlarged view of the device 3602 when it is in a partially deployed position. FIG. 23D illustrates a cross section of the radioactive coil member 3608 taken normal to a central longitudinal axis of the coil member 3608 (e.g., taken along line D-D of FIG. 23C), while FIG. 23E illustrates a cross section taken along the longitudinal axis of the coil member 3608. As can be seen in these views, in one embodiment, the coil member 3608 may be an elongate tube having both a first lumen 3614 and a second lumen 3616 that extend through the elongate tube between the sleeves 3612. The first lumen 3614 may house a radiation source, e.g., a series of radioactive seeds 108 that may be offset from one another by optional spacers 110, as shown in FIG. 23E, an HDR source (not shown), and the like. The second lumen 3616 may contain a shaping and/or stiffening member, such as shaping wire 3618. The shaping wire 3618 may provide stiffness and twisting resistance to the coil member 3608. In the illustrated embodiment, the shaping wire 3618 (and thus the second lumen 3616) is rectangular in cross section as shown in FIG. 23D. The rectangular shape provides desirable twisting resistance to the radioactive source 3608 during deployment, e.g., it keeps the first lumen 3614 positioned outwardly from the core member 3610 during deployment. However, other shapes are certainly possible without departing from the scope of the invention.

The elongate tube that forms the coil member 3608 may be made from various materials, e.g., extruded fluoropolymers or thermoplastics, similar to the materials described in the applications incorporated by reference herein. The shaping wire 3618 may be made from most any material that can accommodate the helical deployment without undue twisting or permanent deformation. Exemplary materials for the shaping wire include shaped memory alloys such as Nitinol or the like.

Figure 23G:
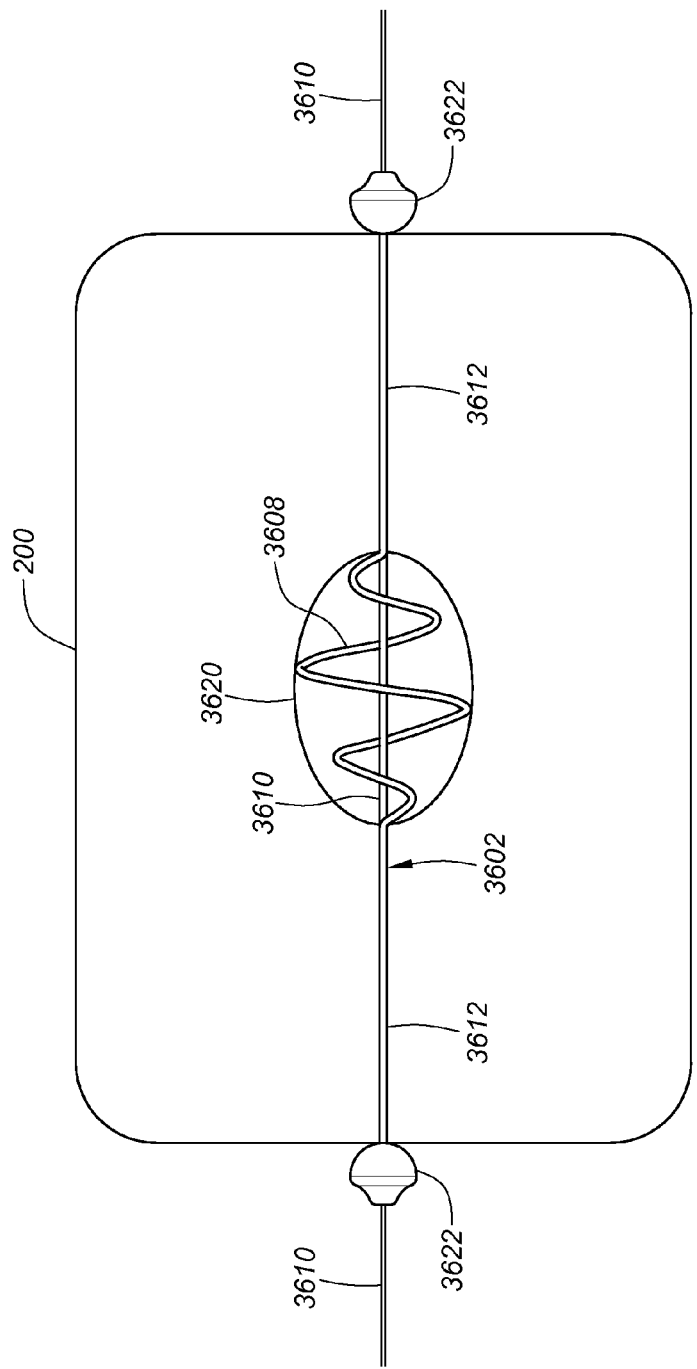

In operation, the device 3602 may be inserted through a tissue structure, e.g., breast 200, while the therapy delivery portion 3604, e.g., coil member 3608, is collapsed along the longitudinal axis of the apparatus 3600. The coil member 3608 may be inserted until it is generally centered in the lumpectomy cavity 3620 as shown in FIG. 23F. The device 3602 may enter through an existing incision (e.g., an incision made at the time of lumpectomy), or it may be placed via a hollow needle (not shown), e.g., as described elsewhere herein and in the applications incorporated by reference herein. Once the device 3602 is generally in place as shown in FIG. 23F, the physician may manipulate (e.g., twist and/or axially displace) the sleeves 3612 that now protrude from each side of the breast 200 to deploy the device 3602. FIG. 23G illustrates the device 3602 as it may be configured when fully deployed within cavity 202. In an exemplary embodiment, the device 3602 may deploy such that the helical coil member 3608 pushes into the cavity walls as already discussed herein (see, e.g., FIGS. 23D-23G) to secure the apparatus 3600 relative to the surrounding tissue.

To secure the device 3602 in place, the physician may fold the sleeves 3612 that extend outside the body against the skin and secure them, e.g., with tape. Alternatively, locking members 3622 may be slid over the ends of the core member 3610. Each locking member 3622 may frictionally engage its respective sleeve 3612 as well as the core member 3610. By securing the sleeves 3612 relative to the core member 3610, the device 3602 may be generally held in place for the course of treatment.

While illustrated herein as utilizing proximal and/or distal sleeves that may protrude outside the body during implantation, other configurations may utilize sleeves that do not protrude. In this case, a tool, e.g., a hollow needle (not shown), may be inserted over the core member to mechanically engage the sleeves and manipulate them as desired (from outside the body) relative to the core member.

Figure 24:
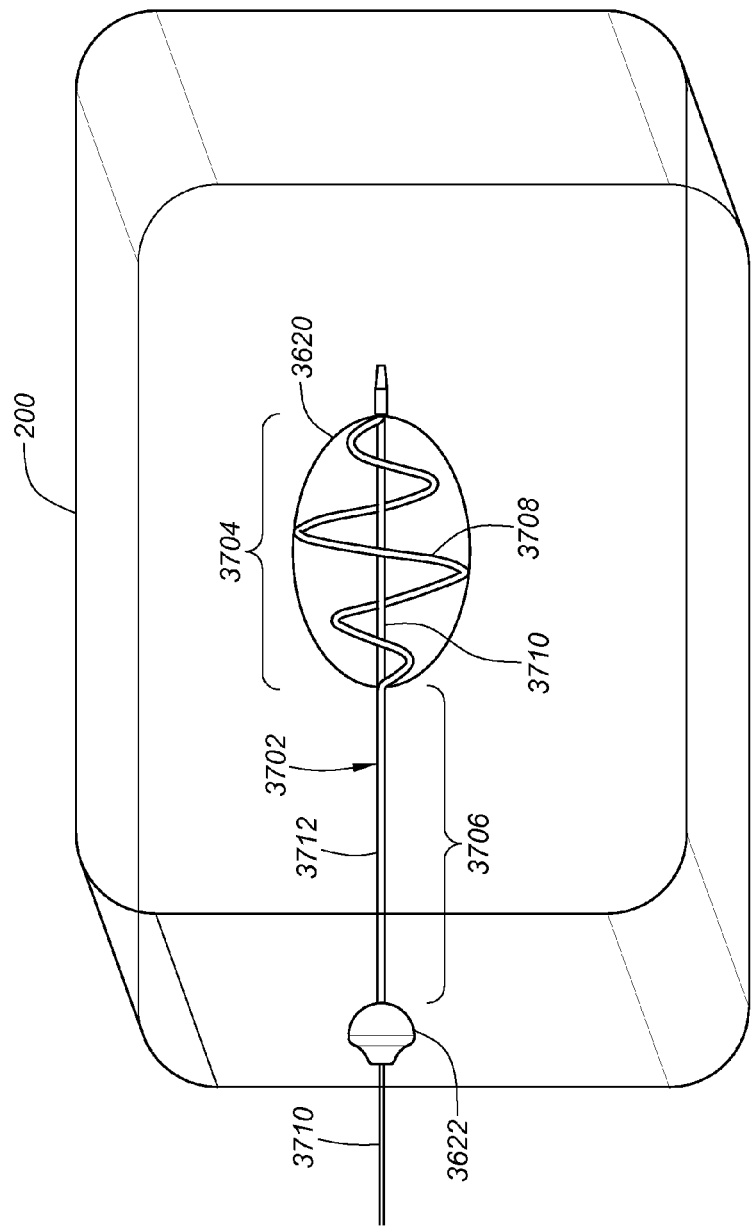
FIG. 24 is a perspective view of a seventh exemplary embodiment of a brachytherapy apparatus including an expandable therapy delivery portion that includes a helical catheter member, showing the apparatus implanted within a lumpectomy cavity of a breast with the helical member in an expanded configuration.

FIG. 24 illustrates a single entry point variation of a brachytherapy device 3702, similar to the device 3602 illustrated in the immediately preceding figures. In this embodiment, a brachytherapy device 3702 is provided having a therapy delivery portion 3704 and a single tail portion 3706. The therapy delivery portion 3704 may be configured as a coil member 3708 substantially similar in construction to the coil member 3608 described above (e.g., helically wound around a core member 3710). The tail portion 3706 may also be formed by a sleeve 3712 similar in most respects to the sleeves 3612 described above. For example, the sleeve member 3712, which may be coupled to a proximal end of the radioactive source 3608, is operable to slide and/or rotate about the core member 3710.

Unlike the device 3602, a distal end of the coil member 3708 may be attached directly to the core member 3710 at or near its distal end as shown in FIG. 24 such that manipulation of the portion of the core member 3710 located outside the body will effect movement of the distal end of the radioactive source.

In operation, the device 3702 may be inserted, while in a collapsed configuration, through the body (e.g., the breast 200) such that the therapy delivery portion 3704 (e.g., coil member 3708) is positioned within the lumpectomy cavity 3620. The device 3702 may enter through an existing incision (e.g., made at the time of lumpectomy) or, it may be placed via a needle (not shown), e.g., as described elsewhere herein with respect to other embodiments. Once the device 3702 is generally in place as shown in FIG. 24, the physician may manipulate both the sleeve 3712 and the core member 3710 that both protrude from a proximal side of the breast 200. For example, axial displacement of the sleeve 3712 towards the distal end of the core member 3710 while rotating the core member 3710 (which is fixed to the distal end of the coil member 3708) may deploy central portions of the coil member 3708 away from the core member 3710 to an expanded configuration, as shown in FIG. 24 (once again, the device 3702 may expand into the tissue as already described herein). The device 3702 may be secured in the deployed configuration in the same manner as described above with respect to the device 3602, e.g., with locking member 3622.

In an alternate embodiment to any of the apparatus herein, one or more helical elongate members may be provided on a core member such that resulting apparatus includes an inner layer, e.g., one or more helical members expandable to a first diameter (not shown), and an outer layer, e.g., one or more helical members expandable to a second diameter larger than the first diameter. In this alternative, these dual layer devices allow for an additional radial layer of radiation to be delivered. When combined with tissue invagination, these dual layers provide multiple shells or layers of dose clouds that may enshroud a significant thickness of breast tissue that curves around a given lumpectomy cavity, e.g., as described in the applications incorporated by reference herein.

The apparatus described herein may permit brachytherapy devices (or other radiation sources), via a single point of entry, to deliver radiation to the tissue surrounding a cavity from a position within the cavity. Moreover, the intracavitary apparatus, methods, and systems described herein may permit substantial fixation of one or more radioactive sources relative to the target tissue surrounding the cavity. The surrounding tissue may invaginate sufficiently around the devices to ensure adequate fixation and/or sufficient depth of penetration of the desired radiation dose to the tissue adjacent the lumpectomy cavity throughout the implantation period. As a result, the desired dose delivery to specific tissue may be achieved over the course of brachytherapy treatment. Moreover, irradiation of unintended tissue, e.g., due to movement of the device relative to the surrounding tissue, may be minimized.

The brachytherapy devices described herein may be implanted into (and/or around) a tumor before surgical excision (neoadjuvantly), and then subsequently removed before or at the time of surgery. Such treatments may shrink or even destroy the tumor. In other embodiments, the apparatus and methods described herein may be used to deliver brachytherapy after surgically removing tumor tissue to treat surrounding tissue post-operatively (post-lumpectomy in breast). In some instances, it is contemplated that brachytherapy apparatus and methods described and illustrated herein may supplement or reduce the need for conventional treatment options, e.g., tumor excision, full field external beam radiation therapy (EBRT), and chemotherapy. Alternatively, the methods described herein may be performed adjuvantly with these and other treatments, e.g., with chemotherapy, EBRT.

Treatment in accordance with the present invention may also avoid some of the disadvantages of HDR treatment, e.g., high activity, exposure of unintended tissue, potentially bulky and protruding catheters, and/or the need for numerous patient visits to receive treatment. Alternatively, the apparatus and methods described herein may be used to perform HDR treatment, e.g., by delivering one or more HDR radiation sources along pathways of the devices in accordance with known HDR dose plans. In a further alternative, a HDR radiation source (e.g., an Iridium tipped afterloader cable from Varian Medical Systems, Inc., or a small diameter x-ray source, such as those disclosed in U.S. Publication No. 2005/0061533A1, the disclosure of which is expressly incorporated by reference herein) may be advanced through any of the core members described herein, with the expandable devices opening a cavity to facilitate delivering radiation more evenly to the tissue surrounding the cavity. Optionally, the core member may shield the radiation source to direct radiation from the radiation source towards a desired portion of the surrounding tissue.

The brachytherapy devices described herein are also substantially flexible, in comparison to conventional HDR catheters, such that they may be placed in either a straight or curvilinear (e.g., curved or spiral) fashion. Such flexibility may permit implantation of radiation sources (e.g., seeds) in configurations and locations that otherwise may be considered inaccessible.

Apparatus and methods of the present invention may also potentially achieve desired dosage with relatively few catheters. For example, the apparatus and methods described herein potentially may obtain desired dose delivery levels with fewer catheters per target than is typically utilized with conventional HDR methods. Yet, the devices described herein may still be implanted with the use of conventional imaging methods (e.g. stereotactic X-ray, ultrasound, CT).

Apparatus and methods of the present invention may also provide other benefits to the patient. For example, potentially less skin damage and discomfort may result from smaller and more flexible catheter insertions. Further, the small flexible tail portions, once in their proper position, may be trimmed short, but may also be folded and taped against the skin, unlike rigid HDR catheters. Thus, the patient may have less discomfort over the course of treatment and potentially improved post-procedural cosmesis. Further, for example, apparatus and techniques in accordance with the present invention may potentially result in reduced side effects as compared to other treatments, e.g., EBRT and chemo, and may require fewer hospital visits over the course of the treatment regimen as compared to, for example, current HDR brachytherapy.

Still further, the brachytherapy delivery systems described herein may provide a standardized dose of radiation based upon lesion size. As a result, the need for extensive dose calculating and mapping systems may potentially be reduced or eliminated with certain cancers (e.g., breast).

The complete disclosure of the patents, patent documents, and publications cited in the Background, the Detailed Description of Exemplary Embodiments, and elsewhere herein are incorporated by reference in their entirety as if each were individually incorporated. Additional information on brachytherapy apparatus that include features that may be incorporated into the embodiments described herein and on methods for using such apparatus may be found in application Ser. No. 10/658,518, filed Sep. 9, 2003, now issued as U.S. Pat. No. 7,601,113, 60/731,879, filed Oct. 31, 2005, and 60/735,532, filed Nov. 10, 2005, Ser. No. 11/276,851, filed Mar. 16, 2006, now issued as U.S. Pat. No. 7,862,496, 60/803,828, filed Jun. 2, 2006, 60/828,655, filed Oct. 8, 2006, and 61/089,855, filed Aug. 18, 2008. The entire disclosures of these applications are expressly incorporated by reference herein.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A brachytherapy treatment apparatus, comprising:
   an elongate core member comprising a proximal end and a distal end configured for introduction into a tract through tissue and terminating in a distal tip;
   an outer member surrounding a portion of the core member proximal to the distal tip and movable relative to the core member;
   a plurality of helical members, each helical member comprising a distal end coupled to the core member distal end, a proximal end coupled to the outer member, an elongate portion that extends helically in a first helical direction around the core member between the helical member proximal and distal ends such that the helical members do not overlap one another, and a pathway extending between the helical member proximal and distal ends for receiving a source of radiation therealong, the outer member being actuatable for moving the helical members from a collapsed configuration to an expanded configuration such that each elongate portion is directed radially outwardly away from the core member; and a balloon comprising a proximal end coupled to the outer member and a distal end coupled to the distal tip of the core member such that the balloon surrounds at least a portion of the core member distal end, the helical members extending helically around and outside an outer surface of the balloon and uncoupled from the balloon such that the helical members are expandable independently of the balloon, wherein the helical members comprise a pair of helical members extending in the first helical direction and offset from one another such that the helical members do not overlap one another in the collapsed configuration.

2. The apparatus of claim 1, further comprising a distal hub coupled to the distal tip of the core member, the distal end of each helical member coupled to the distal hub.

3. The apparatus of claim 1, wherein the outer member comprises a proximal hub movably mounted on the core member and an actuator member extending proximally from the proximal hub, the actuator member movable from adjacent the core member proximal end for actuating the proximal hub to direct the helical members from the collapsed configuration to the expanded configuration.

4. The apparatus of claim 3, wherein the actuator member is movable axially for directing the proximal hub axially to direct the helical members from the collapsed configuration to the expanded configuration.

5. The apparatus of claim 3, wherein the actuator member is movable rotationally for rotating the proximal hub to direct the helical members from the collapsed configuration to the expanded configuration.

6. The apparatus of claim 3, wherein the actuator member comprises a tubular member comprising a distal end coupled to the proximal hub and a proximal end disposed adjacent the core member proximal end.

7. The apparatus of claim 3, wherein the actuator member comprises one or more detents on the actuator member proximal end for releasably securing the actuator member in a first position when the helical members have been directed to the expanded configuration.

8. The apparatus of claim 7, wherein the core member comprises a first detent on the core member proximal end that engages the one or more detents on the actuator member for releasably securing the actuator member in the first position.

9. The apparatus of claim 8, wherein the core member comprises a second detent on the core member proximal end that engages the one or more detents on the actuator member for releasably securing the actuator member in a second position when the helical members have been directed to the collapsed configuration.

10. The apparatus of claim 9, wherein the second detent is located proximal to the first detent on the core member proximal end.

11. The apparatus of claim 8, wherein the first detent limits movement of the actuator member relative to the core member to limit a maximum size of the helical members in the expanded configuration.

12. The apparatus of claim 1, wherein the core member comprises a pathway for receiving a source of radiation.

13. The apparatus of claim 1, further comprising a source of radiation introduceable along the pathway of each helical member for delivering radiation to a target location accessed via the tract through tissue.

14. The apparatus of claim 1, wherein each helical member comprises a tubular member and an elongate support for biasing the tubular member to maintain a helical shape when the helical member is directed between the collapsed and expanded configurations.

15. The apparatus of claim 14, wherein the elongate support is biased to a helical shape corresponding to the expanded configuration, the elongate support being elastically compressible inwardly when the helical member is directed towards the collapsed configuration.

16. The apparatus of claim 14, wherein the elongate support is biased to a helical shape corresponding to the collapsed configuration, the elongate support being elastically expandable outwardly when the helical member is directed towards the expanded configuration.

17. The apparatus of claim 14, wherein the support extends along an outer surface of the tubular member.

18. The apparatus of claim 17, wherein the support is attached to the outer surface of the tubular member using shrink tubing.

19. The apparatus of claim 1, wherein the pair of helical members are offset from one another about one hundred eight degrees around a perimeter of the core member.

20. A brachytherapy treatment apparatus comprising:
an elongate core member comprising a proximal end and a distal end configured for introduction into a tract through tissue and terminating in a distal tip;
an outer member surrounding a portion of the core member proximal to the distal tip and movable relative to the core member;
a plurality of helical members, each helical member comprising a distal end coupled to the core member distal end, a proximal end coupled to the outer member, an elongate portion that extends helically around the core member between the helical member proximal and distal ends, and a pathway extending between the helical member proximal and distal ends for receiving a source of radiation therealong;
an expandable member comprising a proximal end coupled to the outer member and a distal end coupled to the distal tip of the core member such that the expandable member surrounds at least a portion of the core member distal end, the expandable member uncoupled from the helical members; and
an elongate actuator member coupled to the outer member and movable axially to move the helical members independent of the expandable member from a collapsed configuration where the helical members extend helically around and outside an outer surface of the expandable member to an expanded configuration such that the elongate portions of the helical members are directed radially outwardly away from the expandable member,
wherein the helical members comprise a pair of helical members extending in a first helical direction and offset from one another such that the helical members do not overlap one another in the collapsed configuration.

21. The apparatus of claim 20, wherein the expandable member is expandable independently of the helical members such that the helical members may be expanded away from the expandable member before the expandable member is expanded.

22. The apparatus of claim 20, wherein the core member comprises an inflation lumen extending distally from the core member proximal end and communicating with an interior of the expandable member for delivering inflation media into the interior for expanding the expandable member.

23. The apparatus of claim 20, wherein the pair of helical members are offset from one another about one hundred eight degrees around a perimeter of the core member.

24. The apparatus of claim 20, wherein the expandable member is a balloon.

25. The apparatus of claim 20, further comprising a source of radiation introduceable along the pathway of each helical member for delivering radiation to a target location accessed via the tract through tissue.

26. A brachytherapy treatment apparatus, comprising:
an elongate core member comprising a proximal end and a distal end configured for introduction into a tract through tissue and terminating in a distal tip;
an outer member surrounding a portion of the core member proximal to the distal tip and movable relative to the core member;
a plurality of helical members, each helical member comprising a distal end coupled to the core member distal end, a proximal end coupled to the outer member, an elongate portion that extends helically around the core member between the helical member proximal and distal ends, and a pathway extending between the helical member proximal and distal ends for receiving a source of radiation therealong; and
the outer member being actuatable for moving the helical members from a collapsed configuration to an expanded configuration such that each elongate portion is directed radially outwardly away from the core member,
wherein the helical members are configured such that adjacent windings of the helical members are spaced apart axially from one another by no more than one and a half centimeters.

27. The apparatus of claim 26, further comprising a distal hub coupled to the distal tip of the core member, the distal end of each helical member coupled to the distal hub.

28. The apparatus of claim 26, wherein the outer member comprises a proximal hub movably mounted on the core member and an actuator member extending proximally from the proximal hub, the actuator member movable from adjacent the core member proximal end for actuating the proximal hub to direct the helical members from the collapsed configuration to the expanded configuration.

29. The apparatus of claim 28, wherein the actuator member is movable axially for directing the proximal hub axially to direct the helical members from the collapsed configuration to the expanded configuration.

30. The apparatus of claim 28, wherein the actuator member is movable rotationally for rotating the proximal hub to direct the helical members from the collapsed configuration to the expanded configuration.

31. The apparatus of claim 26, wherein the core member comprises a pathway for receiving a source of radiation.

32. The apparatus of claim 26, wherein each helical member comprises a tubular member and an elongate support for biasing the tubular member to maintain a helical shape when the helical member is directed between the collapsed and expanded configurations.

33. The apparatus of claim 26, further comprising a source of radiation introduceable along the pathway of each helical member for delivering radiation to a target location accessed via the tract through tissue.

* * * * *